US011767317B1

(12) United States Patent
Navarre et al.

(10) Patent No.: US 11,767,317 B1
(45) Date of Patent: Sep. 26, 2023

(54) METHODS OF SYNTHESIZING ENANTIOPURE DEUTERIUM-ENRICHED PIOGLITAZONE

(71) Applicant: Poxel SA, Lyons (FR)

(72) Inventors: Laure Françoise Valérie Navarre, Lyons (FR); Vincent Jacques, Somerville, MA (US); Sébastien Bolze, Massieux (FR)

(73) Assignee: Poxel SA, Lyons (FR)

( * ) Notice: Subject to any disclaimer, the term of this patent is extended or adjusted under 35 U.S.C. 154(b) by 13 days.

(21) Appl. No.: 17/360,315

(22) Filed: Jun. 28, 2021

Related U.S. Application Data

(60) Provisional application No. 63/081,732, filed on Sep. 22, 2020, provisional application No. 63/046,336, filed on Jun. 30, 2020.

(51) Int. Cl.
*C07D 417/12* (2006.01)
*C07B 59/00* (2006.01)

(52) U.S. Cl.
CPC .......... *C07D 417/12* (2013.01); *C07B 59/002* (2013.01); *C07B 2200/05* (2013.01)

(58) Field of Classification Search
CPC .................................................. C07D 471/12
See application file for complete search history.

(56) References Cited

U.S. PATENT DOCUMENTS

| | | | |
|---|---|---|---|
| 4,421,865 A | 12/1983 | Shen | |
| 4,687,777 A | 8/1987 | Meguro et al. | |
| 5,134,127 A | 7/1992 | Stella et al. | |
| 5,149,820 A | 9/1992 | Borretzen et al. | |
| 5,441,971 A | 8/1995 | Sohda et al. | |
| 6,191,154 B1 | 2/2001 | Landreth et al. | |
| 6,221,335 B1 | 4/2001 | Foster | |
| 6,334,997 B1 | 1/2002 | Foster et al. | |
| 6,432,993 B1 | 8/2002 | Fujita et al. | |
| 6,440,710 B1 | 8/2002 | Keinan et al. | |
| 6,603,008 B1 | 8/2003 | Ando et al. | |
| 6,706,746 B2 | 3/2004 | Fujita et al. | |
| 7,517,990 B2 | 4/2009 | Ito et al. | |
| 8,067,450 B2 | 11/2011 | Colca et al. | |
| 8,236,786 B2 | 8/2012 | Finch et al. | |
| 8,263,631 B2 | 9/2012 | Fujiwara et al. | |
| 8,389,556 B2 | 3/2013 | Colca et al. | |
| 8,722,710 B2 | 5/2014 | Czarnik | |
| 8,969,581 B2 | 3/2015 | DeWitt | |
| 9,123,444 B2 | 9/2015 | Subramaniam et al. | |
| 9,416,117 B2 | 8/2016 | DeWitt | |
| 9,782,395 B2 | 10/2017 | Collazo et al. | |
| 9,833,445 B2 | 12/2017 | DeWitt | |
| 9,925,175 B2 | 3/2018 | Czarnik | |
| 10,188,639 B2 | 1/2019 | DeWitt et al. | |
| 2003/0181494 A1 | 9/2003 | Neogi et al. | |
| 2004/0253180 A1 | 12/2004 | Foster et al. | |
| 2007/0082929 A1 | 4/2007 | Gant et al. | |
| 2007/0197695 A1 | 8/2007 | Potyen et al. | |
| 2009/0028868 A1 | 1/2009 | Fujiwara et al. | |
| 2009/0076093 A1 | 3/2009 | Czarnik | |
| 2009/0082405 A1* | 3/2009 | Czarnik | A61K 31/4439 514/342 |
| 2012/0015982 A1 | 1/2012 | Colca et al. | |
| 2014/0221369 A1 | 8/2014 | DeWitt | |
| 2014/0243377 A1 | 8/2014 | Czarnik | |
| 2014/0275180 A1 | 9/2014 | DeWitt | |
| 2015/0284346 A1 | 10/2015 | DeWitt | |
| 2016/0331737 A1 | 11/2016 | DeWitt et al. | |
| 2016/0354355 A1 | 12/2016 | Czarnik | |
| 2017/0049762 A1 | 2/2017 | DeWitt | |
| 2018/0117026 A1 | 5/2018 | DeWitt et al. | |
| 2018/0118730 A1 | 5/2018 | DeWitt et al. | |
| 2018/0125827 A1 | 5/2018 | DeWitt et al. | |
| 2018/0125834 A1 | 5/2018 | DeWitt et al. | |
| 2018/0133204 A1 | 5/2018 | DeWitt | |
| 2019/0269665 A1 | 9/2019 | DeWitt et al. | |

(Continued)

FOREIGN PATENT DOCUMENTS

EP 1628646 B1 7/2010
WO 92/018501 A1 10/1992

(Continued)

OTHER PUBLICATIONS

U.S. Appl. No. 12/233,751, filed Sep. 19, 2008, Czarnik, Anthony W.
U.S. Appl. No. 16/531,812, filed Aug. 5, 2019, Czarnik, Anthony W.
U.S. Appl. No. 17/166,588, filed Feb. 3, 2021, Czarnik, Anthony W.
U.S. Appl. No. 14/272,761, filed May 8, 2014, Czarnik, Anthony W.
U.S. Appl. No. 15/088,472, filed Apr. 1, 2016, Czarnik, Anthony W.
U.S. Appl. No. 15/917,983, filed Mar. 12, 2018, Czarnik, Anthony W.
U.S. Appl. No. 15/109,533, filed Oct. 7, 2016, Dewitt, Sheila et al.
U.S. Appl. No. 16/211,488, filed Dec. 6, 2018, Dewitt, Sheila et al.
Kahn, et al., "Unraveling the mechanism of action of thiazolidinediones," J. Clin. Invest. 2000, 106, 1305-1307.
Norris, et al., "Muscle-specific PPAR?-deficient mice develop increased adiposity and insulin resistance but respond to thiazolidinediones," J. Clin Invest 2003, 112, 608-618.

(Continued)

*Primary Examiner* — Matthew P Coughlin
(74) *Attorney, Agent, or Firm* — Goodwin Procter LLP

(57) ABSTRACT

The invention provides methods of synthesis of enantiopure deuterium enriched R-pioglitazone with structure of compound (IV), or a pharmaceutically acceptable salt thereof:

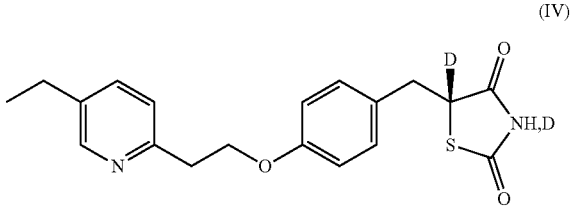

(IV)

The invention further provides chemical intermediates useful in the synthesis of compound (IV), and methods of synthesizing those intermediates.

20 Claims, 11 Drawing Sheets

(56) References Cited

U.S. PATENT DOCUMENTS

| | | | |
|---|---|---|---|
| 2020/0179360 A1 | 6/2020 | Czamik | |
| 2021/0403464 A1* | 12/2021 | Navarre | A61P 3/10 |

FOREIGN PATENT DOCUMENTS

| | | | | |
|---|---|---|---|---|
| WO | 1995/26325 A2 | 10/1995 | | |
| WO | 1999/018081 A1 | 4/1999 | | |
| WO | 2003/033494 A1 | 4/2003 | | |
| WO | 2003/059271 A2 | 7/2003 | | |
| WO | 2004/073622 A2 | 9/2004 | | |
| WO | 2005/058827 A1 | 6/2005 | | |
| WO | 2006/064826 A1 | 6/2006 | | |
| WO | 2006/083781 A1 | 8/2006 | | |
| WO | 2006/126673 A1 | 11/2006 | | |
| WO | 2007/007656 A1 | 1/2007 | | |
| WO | 2007/100027 A1 | 9/2007 | | |
| WO | 2007/109024 A2 | 9/2007 | | |
| WO | 2007/136129 A1 | 11/2007 | | |
| WO | 2008/099944 A1 | 8/2008 | | |
| WO | 2009/038681 A1 | 3/2009 | | |
| WO | 2010/015818 A1 | 2/2010 | | |
| WO | 2010/150014 A1 | 12/2010 | | |
| WO | WO-2010150014 A1 * | 12/2010 | | A61K 31/426 |
| WO | 2011/017244 A1 | 2/2011 | | |
| WO | 2011/065420 A1 | 6/2011 | | |
| WO | 2011/098799 A2 | 8/2011 | | |
| WO | 2011/098801 A1 | 8/2011 | | |
| WO | 2011/100685 A2 | 8/2011 | | |
| WO | 2011/133441 A2 | 10/2011 | | |
| WO | 2013/011402 A1 | 1/2013 | | |
| WO | 2013/056232 A2 | 4/2013 | | |
| WO | 2013/134626 A1 | 9/2013 | | |
| WO | 2014/121036 A1 | 8/2014 | | |
| WO | 2014/152843 A1 | 9/2014 | | |
| WO | 2015/109037 A1 | 7/2015 | | |
| WO | 2016153948 A1 | 9/2016 | | |

OTHER PUBLICATIONS

Lehmann, et al., "An Antidiabetic Thiazolidinedione Is a High Affinity Ligand for Peroxisome Proliferator-activated Receptor ? (PPAR?)*," J Biol Chem 1995, 270, 12953-12956, Nat Med 2013, 19, 557-566.

Wang, et al., "Peroxisome Prolifterator-Activated Receptor ? and Its Role in Adipocyte Homeostatis and Thiazolidinedione-Mediated Insulin Sensitation," Mol Cell Biol 2018, 38, e00677-17.

Ahmadian, et al., "PPAR? signaling and metabolism: the good, the bad and the future," Nat Med 2013, 19, 557-66.

Zhang et al., A Newly Discovered Racemic Compound of Pioglitazone Hydrochloride Is More Stable than the Commercial Conglomerate, Jan. 21, 2019, pp. 414-417.

Czarnik, et al., "Characterizing the non-PPAR? Mitochondrial Function Modulation & Anti-inflammatory Activity of Thiazolidinedione (TZD) Enantiomers using Deuterium," Discovery of DRX-065, Aug. 24, 2016, pp. 1-30.

Klussmann, et al., "Rationalization and Prediction of Solution Enantiomeric Excess in Ternary Phase Systems," Angew. Chem. Int. Ed. 2006,45, pp. 7985-7989.

Coquerel, "Solubility of chiral species as function of the enantiomeric excess," 2015 Royal Pharmaceutical Society, Journal of Pharmacy and Pharmacology, 67, pp. 869-878.

Srisanga, et al., "Racemic Compound, Conglomerate, or Solid Solution: Phase Diagram Screening of Chiral Compounds," 2010 American Chemical Society, pp. 1808-1812.

PCT/US2010/150014 International Search Report dated Aug. 24, 2010.

PCT/US2010/015818 International Search Report dated Oct. 11, 2009.

Jacques, et al., "Safety, Tolerability and Pharmacokinetics of DRX-065, the Stabilized, Preferred R-Stereoisomer of Pioglitazone: A Mitochondrial Function Modulator for Nonalcoholic Steatohepatitis (NASH) without the PPAR? Agonism and Related Side Effects of Pioglitazone," Abstract Poster, Hepatology 2018, vol. 68 Issue S1 (Oct. 1, 2018), 964A.

Bolze, et al., "Phase 1 Study of PXL065 Confirms Dose-Proportionality & Stabilization Of The Preferred Stereoisomer (R-Pioglitazone) for the Treatment of NASH," Hepatology 2019, Abstract Poster, vol. 70 Issue S1 (Oct. 1, 2019), 1264A-1265A.

Bolze, et al., "Phase 1b Study Of PXL065 (Deuterium-Stabilized R-Pioglitazone), a Novel NASH Candidate, Predicts 15mg Equivalent to 45mg Actos®," Abstract Poster, Hepatology 2020, vol. 72 Issue S1 (Oct. 1, 2020), 1055A-1056A.

Bharatam et al., "Rapid Racemization in Thiazolidinediones: A Quantum Chemical Study", J. Phys. Chem. A., 108:3784-3788 (2004).

Buteau, K., "Deuterated Drugs: Unexpectedly Nonobvious?", 10 J. High Tech. L. 22 (2009) (53 pages).

Cabrero et al., "Peroxisome Proliferator-Activated Receptors and the Control of Inflammation", Current Drug Target-Inflammation & Allergy, 1(3):243-248 (2002) (Abstract).

Chen et al., "Insulin Resistance and Metabolic Derangements in Obese Mice Are Ameliorated by a Novel Peroxisome Proliferator-activated Receptor g-sparing Thiazolidinedione", J. Biol. Chem., 287(28):23537-23548 (2012).

Colca et al., "Identification of a Mitochondrial Target of Thiazolidinedione Insulin Sensitizers (mTOT)-Relationship to Newly Identified Mitochondrial Pyruvate Carrier Proteins", PLOS One, 8(5)e61551:1-10 (2013).

Colca et al., "Identification of a Novel Mitochondrial Protein ("mitoNEET") Cross-linked Specifically by a Thiazolidinedione Photoprobe," Am. J. Physiol. Endocrinol. Metab. (2004) vol. 286, No. 2, pp. E252-E260.

Divakaruni et al.," I hiazolidinediones are Acute, Specific Inhibitors of the Mitochondrial Pyruvate Carrier," Proc Natl Acad Sci USA, (2013), 110(14):5422-7.

Federal Register "Examination guidelines" p. 1-34, Sep. 1, 2010.

Fisher et al., "The complexities inherent in attempts to decrease drug clearance by blocking sites of CYP-mediated metabolism", Curr. Opin. Drug Disc. Dev., 9(1):101-109 (2006).

Foster, A., "Deuterium Isotope Effects in the Metabolism of Drugs and Xenobiotics: Implications for Drug Design", Adv. Drug Res., 14:2-40 (1985).

Foster, "Deuterium Isotope Effects in Studies of Drug Metabolism," Trends Pharmacol Sci, (1984), 5:524-7.

Harbeson et al., "Deuterium in Drug Discovery and Development", Annual Reports in Med Chem, 46:403-417 (2011).

Hutt et al., "The Chiral Switch: The Development of Single Enantiomer Drugs from Racemates", ACTA Facult. Pharm. Univ. Comenianae, 50:7-23 (2003).

PCT/US2014/014083 International Search Report and Written Opinion dated May 16, 2014 (12 pages).

PCT/US2014/027943 International Search Report and Written Opinion dated Jul. 10, 2014 (15 pages).

Jaakkola et al., "Pioglitazone is Metabolized by CYP2C8 and CYP3A4 in vitro. Potential for Interactions with CYP2C8 Inhibitors," Basic Clin Phamacol Toxicol, (2006), 99(1):44-51.

Jaakkola et al., "Montelukast and Zafidukast do not Affect the Pharmacokinetics of the CYP2C8 Substrate Pioglitazone," Eur J Clin Pharmacol, (2006), 62(7):503-9.

Jamali et al., "Investigation of racemisation of the enantiomers of glitazone drug compounds at different pH using chiral HPLC and chiral Ce", J. Pharm and Biomed Anal., 46:82-87 (2008).

Kaufman et al., "Deuterium Enrichment of Vitamin A at the C20 Position Slows the Formation of Detrimental Vitamin A Dimers in Wild-type Rodents", J Biol. Chem., 286(10):7958-7965 (2011).

Kushner, D.J. et al. "Pharmacological Uses and Perspectives of Heavy Water and Deuterated Compounds," Canadian Journal of Physiology and Pharmacology, 1999, 77(2), 79-88.

Maltais et al., "In Vitro and In Vivo Isotope Effects with Hepatitis C Protease Inhibitors: Enhanced Plasma Exposure of Deuterated Telaprevir versus Telaprevir in Rats", J. Med. Chem. (2009) vol. 52, pp. 7993-8001.

(56) References Cited

OTHER PUBLICATIONS

Mislow et al., "A Note on Steric Isotope Effects. Conformational Kinetic Isotope Effects in the Racemization of 9,10-Dihydro-4-5-Dimethylphenanthrene", J. Am. Chem. Soc. 85:1199-1200 (1963).
Motani et al., "INT131: A Selective Modulator of PPARg", J. Mol. Biol., 386:1301-1311 (2009).
Nassar et al., "Improving the decision-making process in the structural modification of drug candidates: enhancing metabolic stability", Drug Discovery Today, 9(23):1020-1028 (2004).
Nelson et al., "The Use of Deuterium Isotope Effects to Probe the Active Site Properties, Mechanism of Cytochrome P450-Catalyzed Reactions, and Mechanisms of Metabolically Dependent Toxicity", Drug Metabolism and Disposition, 31(12):1481-1498 (2003).
Parks et al., "Differential Activity of Rosiglitazone Enantiomers at PPARg", Bioorg. & Medicinal Chem. Letters, 8:3657-3658 (1998).
Pfutzner et al., "Pioglitazone: update on an oral antidiabetic drug with antiatherosclerotic effects", Expert Opin. Pharmacother., 8(12):1985-1998 (2007).
Shao et al., "Derivatives of tramadol for increased duration of effect", Bioorg. Med. Chem. Lett. 16:691-694 (2006).
Shao, L. & Hewitt, M.C. "The Kinetic Isotope Effect in the Search for Deuterated Drugs," Drug News & Perspectives, 2010, vol. 23, No. 6, pp. 398-404.
Sohda et al., "Studies on Antidiabetic Agents. XII.1) Synthesis and Activity of the metabolites of (±)-5-[p-[2-(5-Ethyl-2-pyridyl)ethoxy]benzyl]-2,4-thiazolidinedione (Pioglitazone)", Chem. Pharm. Bull., 43(12):2168 2172 (1995).
Stedman and Barclay, "Review Article: Comparison of the Pharmacokinetics, Acid Suppression and Efficacy of Proton Pump Inhibitors," Aliment Pharmacol Ther, (2000), 14(8):963-78.
Wade, D., "Deuterium isotope effects on noncovalent interactions between molecules", Chemico-Biological Interactions, 117 p. 191-217 (1999).
Wiberg, K., "The Deuterium Isotope Effect", Chem. Rev., 55(4):713-743 (1955).
Yamamoto et al., "Synthesis and Configurational Stability of (S)- and (R)-Deuteriothalidomides", Chem. Pharm. Bull. 58(1):110-112(2010).
Yarnell, A., "Heavy-Hydrogen Drugs Turn Heads, Again", Chemical & Engineering News, 87(25):36-39 (2009).
Zhu Y. et al., "Deuterated Clopidogrel Analogues as a New Generation of Antiplatelet Agents", ACS Med. Chem. Lett. 2013, vol. 4, Issue 3, pp. 349-352.
Baillie, T., "The Use of Stable Isotopes in Pharmacological Research", Pharmacological Reviews, 33(2):81-132 (1981).
Browne, T., "Stable Isotope Techniques in Early Drug Development: An Economic Evaluation", J Clin Pharmacol, 38:213-220 (1998).
Cherrah et al., "Study of Deuterium Isotope Effects on Protein Binding by Gas Chromatography/Mass Spectrometry. Caffeine and Deuterated Isotopomers", Biomedical and Environmental Mass Spectrometry, 14:653-657 (1987).
Dyck et al., "Effects of Deuterium Substitution on the Catabolism of β-Phenylethylamine: An In Vivo Study", J Neurochem, 46(2):399-404 (1986).
Gouyette, A., "Synthesis of Deuterium-labelled Elliptinium and its Use in Metabolic Studies", Biomedical and Environmental Mass Spectrometry, 15:243-247 (1988).
Haskins, N. J. "The Application of Stable Isotopes in Biomedical Research," Biomedical Mass Spectrometry, 9 (7), 1982, 269-277.
Honma et al., "The Metabolism of Roxatidine Acetate Hydrochloride", Drug Metabolism and Disposition, 15(4):551-559 (1987).
Pieniaszek, Jr., et al., "Moricizine Bioavailability via Simultaneous, Dual, Stable Isotope Administration: Bioequivalence Implications", J Clin Pharmacol, 39:817-825 (1999).
Tonn et al. "Simultaneous Analysis of Diphenhydramine and a Stable Isotope Analog (2H10)Diphenydramine Using Capillary Gas Chromatography with Mass Selective Detection in Biological Fluids from Chronically Instrumented Pregnant Ewes," Biological Mass Spectrometry, 22 (11) 1993, 633-642.
Nolen, R. L. "The application of stable isotopes to studies of drug bioavailability and bioequivalence," J. Clin. Pharm. (1986) vol. 26, pp. 419-424.
Aithal et al., "Randomized, Placebo-Controlled Trial of Pioglitazone in Nondiabetic Subjects with Nonalcoholic Steatohepatitis," Gastroenterology (2008), vol. 135, pp. 1176-1184.
Boettcher et al., "Meta-analysis: Pioglitazone Improves Liver Histology and Fibrosis in Patients with Non-Alcoholic Steatohepatitis," Aliment Pharmacol Ther, vol. 35, pp. 66-75 (2012).
Federico, et al., "Focus on emerging drugs for the treatment of patients with non-alcoholic fatty liver disease," World Journal of Gastroenterology (2014), vol. 20, pp. 16841-16857.
Kawaguchi et al., "Pioglitazone prevents hepatic steatosis, fibrosis, and enzyme-altered lesions in rat liver cirrhosis induced by a choline-deficient L-amino acid-defined diet," Biochemical and Biophysical Research Communications, (2004), vol. 315, pp. 187-195.
Kawai et al., "Hydrogen-Rich Water Prevents Progression of Nonalcoholic Steatohepatitis and Accompanying Hepatocarcinogenesis in Mice," Hepatology (2012), vol. 56, pp. 912-921.
Leclercq et al., "Intrahepatic insulin resistance in a murine model of steatohepatitis: effect of PPARg agonist pioglitazone," Laboratory Investigation (2007), vol. 87, pp. 56-65.
Lin et al., "Dose effect of thiazolidinedione on cancer risk in type 2 diabetes mellitus patients: a six-year population-based cohort study," Journal of Clinical Pharmacy and Therapeutics (2014), vol. 39, pp. 354-360.
Lutchman et al., "The Effects of Discontinuing Pioglitazone in Patients with Nonalcoholic Steatohepatitis," Hepatology (2007) vol. 46, pp. 424-429.
Sanyal et al., "Pioglitazone, Vitamin E, or Placebo for Nonalcoholic Steatohepatitis," The New England Journal of Medicine, (2010) vol. 362, pp. 1675-1685.
Sanyal et al., "A Pilot Study of Vitamin E Versus Vitamin E and Pioglitazone for the Treatment of Nonalcoholic Steatohepatitis," Clinical Gastroenterology and Hepatology (2004), vol. 2, pp. 1107-1115.
Uto et al., "The peroxisome proliferator-activated receptor-g agonist, pioglitazone, inhibits fat accumulation and fibrosis in the livers of rats fed a choline-deficient, L-amino acid-defined diet," Hepatology Research (2005), vol. 32, pp. 235-242.
Van Wagner et al., "The role of insulin-sensitizing agents in the treatment of nonalcoholic steatohepatitis," Ther Adv Gastroenterol (2011) vol. 4, pp. 249-263.
Zhang et al., "Thiazolidinediones Improve Hepatic Fibrosis in Rats with Non-Alcoholic Steatohepatitis by Activating the Adenosine Monophosphate-Activated Protein Kinase Signalling Pathway," Clinical and Experimental Pharmacology and Physiology, vol. 39, pp. 1026-1033 (2012).
Tilg and Moschen, "Evolving Therapies for Non-Alcoholic Steatohepatitis," Expert Opin Drug Discov, (2014), 9(6):687-96.
Lomonaco et al., "Nonalcoholic Fatty Liver Disease: Current Issues and Novel Treatment Approaches," Drugs, vol. 73, pp. 1-14 (2013).
Smith et al., "Non-Alcoholic Fatty Liver Disease," Critical Reviews in Clinical Laboratory Sciences, vol. 48, pp. 97-113 (2011).
Dorwald, "Side Reactions in Organic Synthesis," Wiley, pp. IX of preface pp. 1-15 (2005).
Woo, H.Y, et al., "Rescue therapy with adefovir in decompensated liver cirrhosis patients with lamivudine-resistant hepatitis B virus", Clinical and Molecular Hepatology, 2014, vol. 20, pp. 168-176.
Peng, S., et al., "An Updated Meta-Analysis of Randomized Controlled Trials Assessing the Effect of Sorafenib in Advanced Hepatocellular Carcinoma", PLOS ONE, 2014, vol. 9, No. 12, pp. e112530.
Farlow, M. R., et al., "Comparing Clinical Profiles in Alzheimer's Disease and Parkinson's Disease Dementia", Dementia and Geriatric Cognitive Disorders Extra, 2013, vol. 3, pp. 281-290.
Griebeler, M.L., et al., "Pharmacologic interventions for painful diabetic neuropathy: An umbrella systematic review and comparative effectiveness network meta-analysis", Annals of Internal Medicine, 2014, vol. 161, No. 9, pp. 639-649.
Zhou, C. et al., "Discovery of 5-aryloxy-2,4-thiazolidinediones as potent GPR40 agonists", Bioorg. Med. Chem. Lett. 2010, vol. 20, No. 3, pp. 1298-1301.

(56) References Cited

OTHER PUBLICATIONS

Christiansen, E. et al., "Identification of a Potent and Selective Free Fatty Acid Receptor 1 (FFA1/GPR40) Agonist with Favorable Physicochemical and in Vitro ADME Properties", J. Med. Chem. (2011) vol. 54, No. 19, pp. 6691-6703.
PCT/US2015/011493 International Search Report and Written Opinion dated Mar. 6, 2015 (9 pages).
Hardy, T. et al. "Nonalcoholic fatty liver disease: new treatments," Curr. Opin. Gastroenterology (2015) vol. 31, No. 3, pp. 175-183.
Chalasani et al., "The Diagnosis and Management of Non-Alcoholic Fatty Liver Disease: Practice Guideline by the American Gastroenterological Association, American Association for the Study of Liver Diseases, and American College of Gastroenterology," Gastroenterology (2012), vol. 142, No. 7, pp. 1592-1609.
Cusi, K. et al. "Long-Term Pioglitazone Treatment for Patients With Nonalcoholic Steatohepatitis and Prediabetes or Type 2 Diabetes Mellitus: A Randomized, Controlled Trial," Ann. Intern. Med. published online at doi: 10.7326/M15-1774. Published in final form as Ann. Intern. Med. (2016) vol. 165, No. 5, p. 305-315.
Tanis, S. P. et al. "Synthesis and Biological Activity of Metabolites of the Antidiabetic, Antihyperglycemic Agent Pioglitazone," J Med. Chem. (1996) vol. 39, pp. 5053-5063.
Leoni, A. et al., "Novel thiazole derivatives: a patent review (2008-2012. Part 2)," Expert Opin. Ther. Patents (2014), vol. 24, No. 7, pp. 759-777.
Jorden, D., "World Alzheimer Day: French Doctor Denounces Routine Alzheimer Medications," dated Dec. 20, 2015. Downloaded from the Internet at URL: https://zcomm.org/znetarticle/world-alzheimer-day-french-doctor-denounces-routine-alzheimer-medications/ (4 pages).
Landreth, G. et al., "PPARg Agonists as Therapeutics for the Treament of Alzheimer's Disease," Neurotherapeutics: J. Am. Soc. Exper. NeuroTherapeutics (2008), vol. 5, No. 3, pp. 481-489.
Polyzos, S. A. and Mantzoros, C. S. "Adiponectin as a target for the treament of nonalcoholic steatohepatitis with thiazolidinediones: A systematic review," Metabolism, Clinical and Experimental (2016), vol. 65, No. 9, pp. 1297-1306.
World Health Organization "The ICD-10 Classification of Mental and Behavioural Disorders: Diagnostic criteria for research," Geneva (1993).
Venkatesh, S. and Lipper, R. A., "Role of the Development Scientist in Compound Lead Selection and Optimization," J. Pharm. Sci. (2000), vol. 89, No. 2, pp. 145-154.
Mandard, S. and Patsouris, D., "Nuclear Control of the Inflammatory Response in Mammals by Peroxisome Proliferator-Activated Receptors," PPAR Research (2013) Article ID 613864, DOI: 10.1155/2013/613864. (23 pages).
Binda, C. et al., "Molecular Insights into Human Monoamine Oxidase B Inhibition by the Glitazone Antidiabetes Drugs," ACS Med Chem. Lett. (2012), vol. 3, pp. 39-42.
Chalasani et al., "The Diagnosis and Management of Non-Alcoholic Fatly Liver Disease: Practice Guideline by the American Association for the Study of Liver Diseases, American College of Gastroenterology, and the American Gastroenterological Association," Hepatology (2012), vol. 55, No. 6, pp. 2005-2023.
Promrat et al., "A Pilot Study of Pioglitazone Treatment for Non-alcoholic Steatohepatitis," Hepatology (2004), vol. 39, pp. 188-196.
Shadid et al. "Effect of pioglitazone on biochemical indices of non-alcoholic fatty liver disease in upper body obesity," Clinical Gastroenterology and Hepatology, 2003, 1:384-387.
EP 19203107, Supplementary European Search Report, dated Sep. 29, 2020.
Binda, et al., "Molecular insights into human monoamine oxidase B inhibition by the glitazone antidiabetes drugs." ACS medicinal chemistry letters 3, No. 1 (2012): pp. 39-42.
Mehtälä, et al., "Pioglitazone use and risk of bladder cancer: a systematic literature review and meta-analysis of observational studies." Diabetology international 10, No. 1 (2019): pp. 24-36.
Tachibana, et al., "The role of PPARs in cancer." pp. 1-15, PPAR research 2008 (2008).
Tafuri et al., "Effect of Pioglitazone on the Course of New-Onset Type 1 Diabetes Mellitus", Journal of Clinical Research in Pediatric Endocrinology, vol. 5, No. 4, Jan. 1, 2013 (Jan. 1, 2013), pp. 236-239, XP55730567, ISSN: 1308-5727, DOI: 10.4274/Jcrpe.981.
Zardi et al., "Hepatic PPARs: Their Role in Liver Physiology, Fibrosis and Treatment", Current Medicinal Chemistry, 2013, 20,, Jan. 1, 2013 (Jan. 1, 2013), pp. 3370-3396, XP55730602.
Shah et al., "Metformin and Pioglitazone in Polycystic Ovarian Syndrome: A Comparative Study", The Journal of Obstetrics and Gynecology of India, vol. 62, No. 5, Oct. 1, 2012 (Oct. 1, 2012), pp. 551-556, XP055730931.
Paz-Filho et al., "Leptin therapy, insulin sensitivity, and glucose homeostasis", Indian J Endocrinol Metab. Dec. 16, 2012(Suppl 3): S549-S555., Jan. 1, 2012 (Jan. 1, 2012), pp. S549-S555.
Li et al., "Twelve Weeks of Pioglitazone Therapy Significantly Attenuates Dysmetabolism and Reduces Inflammation in Continuous Ambulatory Peritoneal Dialysis Patients-a Randomized Crossover Trial", Perit Dial Int. Sep.-Oct. 2012; 32(5): 507-515, Jan. 1, 2012 (Jan. 1, 2012), pp. 507-515.
Anonymous: "Thiazolidinedione—Wikipedia", Jan. 1, 2013 (Jan. 1, 2013), XP055730935.
LeBrasseur, et al.,"Thiazolidinediones can rapidly activate AMP-activation protein kinase in mammalian tissues," Am. J. Physiol. Endocrinol. Metab. 2006, 291, E175-81.
Feinstein, et al., "Receptor-independent actions of PPAR thiazolidinedione agonists: Is mitochondrial function the key?" Biochem Pharmacol 2005, 70, 177-188.
Bender, et al., "The mitochondrial pyruvate carrier in health and disease: To carry or not to carry?" Biochim. Biophys. Acta—Mol Cell Res, 2016, 1863, 2436-2442.
Brunmair, et al., "Thiazolidinediones, Like Metformin, Inhibit Respiratory Complex I," Diabetes 2004, 53, 1052-1059.
Jacques, et al., "Deuterium-Stabilized (R)-Pioglitazone (PXL065) Is Responsible for Pioglitazone Efficacy in NASH yet Exhibits Little to No PPAR? Activity," Hepatol. Commun. Apr. 10, 2021, doi.org/10.1002/hep4.1723.

\* cited by examiner

| | RT | Name | Area | %Area | USP s/n | USPTailing | USP Plate Count | USP Resolution | s/n |
|---|---|---|---|---|---|---|---|---|---|
| 1 | 3.00 | RRT~ 0.462 | 8382 | 0.10 | 162.6 | 1.35 | 4978 | | 81.8 |
| 2 | 6.50 | PODD-02 | B173706 | 99.62 | 97325.5 | 1.11 | 8383 | 15.02 | 48663.2 |
| 3 | 7.31 | RRT~ 1.126 | 6112 | 0.07 | 45.9 | | | | 23.5 |

| | RT | Name | Area | %Area | USP s/n | USPTailing | USP Plate Count | USP Resolution | s/n |
|---|---|---|---|---|---|---|---|---|---|
| 1 | 20.67 | PODD-03 | 4505437 | 82.07 | 36361.7 | 1.96 | 5260 | | 18181.3 |
| 2 | 23.88 | PODD-03ent | 984310 | 17.93 | 6598.1 | 1.91 | 4622 | 2.53 | 3299.6 |

Peak Results

| | RT | Name | Area | %Area | USP s/n | USPTailing | USP Plate Count | USP Resolution | s/n |
|---|---|---|---|---|---|---|---|---|---|
| 1 | 7.87 | PODD-03 | 9524267 | 99.91 | 30777.0 | 1.11 | 7889 | | 15389.0 |
| 2 | 10.99 | RRT~ 1.396 | 8497 | 0.09 | 17.0 | 1.02 | 4751 | 6.28 | 9.0 |

Peak Results

| | RT | Name | Area | %Area | USP s/n | USPTailing | USP Plate Count | USP Resolution | s/n |
|---|---|---|---|---|---|---|---|---|---|
| 1 | 19.90 | PODD-03 | 5433743 | 96.30 | 43099.0 | 1.82 | 4651 | | 21550.0 |
| 2 | 23.09 | PODD-03ent | 208592 | 3.70 | 1462.1 | 1.46 | 4403 | 2.49 | 731.6 |

| | RT | Name | Area | %Area | USP s/n | USPTailing | USP Plate Count | s/n |
|---|---|---|---|---|---|---|---|---|
| 1 | 7.32 | PODD-04 (PODD-01) | 9969601 | 99.97 | 145900.1 | 1.09 | 8887 | 72950.6 |
| 2 | 8.71 | | 897 | 0.01 | 9.6 | | | 5.3 |
| 3 | 10.53 | | 2530 | 0.03 | 25.4 | 1.07 | 10940 | 13.2 |

Peak Results

| | RT | Name | Area | %Area | USP s/n | USPTailing | USP Plate Count | USP Resolution | s/n |
|---|---|---|---|---|---|---|---|---|---|
| 1 | 5.97 | PXL065 (R-enant) | 43963258 | 98.48 | 283535.9 | 4.23 | 1180 | | 141768.5 |
| 2 | 10.59 | PXL064 (S-enant) | 673340 | 1.52 | 3429.5 | 1.16 | 2162 | 5.71 | 1715.3 |

METHODS OF SYNTHESIZING ENANTIOPURE DEUTERIUM-ENRICHED PIOGLITAZONE

CROSS-REFERENCE TO RELATED APPLICATIONS

This application claims the benefit of and priority to U.S. Provisional Patent Application Ser. No. 63/046,336, filed Jun. 30, 2020, and to U.S. Provisional Patent Application Ser. No. 63/081,732, filed Sep. 22, 2020; the contents of each of which are hereby incorporated by reference in their entirety.

FIELD OF THE INVENTION

The invention provides methods of synthesizing enantiopure deuterium-enriched pioglitazone, which is useful for treating neurological disorders, cancer, respiratory disorders, metabolic disorders, and other disorders using enantiopure deuterium-enriched pioglitazone.

BACKGROUND

Thiazolidinediones (TZDs) are antidiabetic drugs that sensitize the body to insulin. These compounds were empirically discovered to be agonists of peroxisome proliferator-activated-receptors (PPARs), including PPAR-γ (PPARγ), a ligand-activated nuclear receptor that drives broad transcriptional programs associated with adipogenesis, lipid metabolism, innate immune function, and metabolic homeostasis (see, e.g., J. Clin. Invest. 2000, 106, 1305-1307, Trends Endocrinol. Metab. 2012, 23, 205-215). As such, the antidiabetic mechanism of action of TZDs has up to now been attributed to binding to, and activation of, PPARγ (see, e.g., J Biol Chem 1995, 270, 12953-12956, Nat Med 2013, 19, 557-566).

Therapeutics that modulate PPARs have been commercialized for treating medical disorders, such as metabolic disorders. One such example is the TZD, pioglitazone hydrochloride, which has been approved by the United States Food and Drug Administration as an adjunct to diet and exercise to improve glycemic control in adults with type 2 diabetes mellitus in multiple clinical settings. Pioglitazone hydrochloride is marketed under the registered trademark ACTOS® and the prescribing information for ACTOS® explains that pioglitazone is an agonist of PPARγ. PPARγ-related adverse side effects of ACTOS® have been reported including, for example, weight gain, edema and increased incidence of bone fracture.

However, emerging genetic and pharmacologic evidence suggests that TZDs exert many of their beneficial effects independently of PPARγ activation (see Biochem. Pharmacol. 2005, 70, 177-188). For instance, liver and skeletal muscle remain responsive to TZDs despite tissue-specific deletion of PPARγ (see J Clin Invest 2003, 112, 608-618, J Biol Chem 2012, 287, 23537-23548), and the whole-body insulin sensitizing effect of rosiglitazone persists upon PPARγ deletion in mature adipocytes (see Mol Cell Biol 2018, 38, e00677-17). Pharmacologic evidence also suggests TZDs have PPARγ-independent effects. They can acutely alter metabolic homeostasis on a timescale that is likely too rapid to be driven by broad gene expression changes (see Am. J. Physiol. Endocrinol. Metab. 2006, 291, E175-81), and several in vitro and in vivo experiments have shown that rank-order affinity for PPARγ does not always correlate with efficacy (see Biochem. Pharmacol. 2005, 70, 177-188). Pioglitazone and other TZDs have also been shown to have anti-inflammatory activity, which seems to be, at least in part, mediated by a mechanism not involving PPARs (Curr. Drug Targets Inflamm. Allergy 2002, 1, 243-248).

Recent work shows that most of the PPARγ-independent effects of TZDs could be attributed to inhibition of the mitochondrial pyruvate carrier (MPC), an inner mitochondrial membrane transporter responsible for the uptake of glucose-derived pyruvate from the cytoplasm into the mitochondrial matrix (see Biochim. Biophys. Acta—Mol Cell Res, 2016, 1863, 2436-2442). TZDs are acute, specific inhibitors of MPC activity at clinically relevant concentrations (see Proc. Natl. Acad. Sci. USA, 2013, 110, 5422-5427). TZDs also inhibit mitochondrial complex I (see Diabetes 2004, 53, 1052-1059), though at higher and perhaps supraphysiological concentrations relative to the effect on the MPC. Despite pioglitazone decades of use in humans with T2DM, the repertoire of targets for pioglitazone and its exact mechanism of action is only now beginning to be unraveled.

All TZDs, including pioglitazone, are a mixture of stereoisomers and are characterized by the presence of a chiral center. This chiral center is prone to rapid, non-enzymatic inversion of configuration. Thus, the instability of the chiral center has prevented exploitation of the potential for differentiated pharmacology between the enantiomers of TZDs. For example, while the left-handed, or (S)-stereoisomer, of rosiglitazone was identified as the most potent PPARγ agonist, (S)-rosiglitazone rapidly equilibrated to create a 1:1 mixture of (R)- and (S)-rosiglitazone, preventing further in vivo characterization of the stereoisomers (see Bioorg. Med. Chem. Lett., 1998, 8, 3657-8). Furthermore, the anti-inflammatory effects of pioglitazone were shown to be uniquely associated with the (R)-stereoisomer in a rat model of chronic obstructive pulmonary disease. This was achieved only after stabilization of the stereoisomers in an acidic solution, followed by immediate intranasal dosing, which limited inversion during the time course of the study (see patent application WO2010015818).

Due to the increasing number of patients suffering from disorders such as those mentioned above, and the limitations of existing therapies, such as adverse side effects, there is a need for new therapeutic agents for treating medical disorders in which modulation of PPARγ, anti-inflammatory, and/or MPC activity are predicted to be beneficial.

The use of deuterium-enriched derivatives of pioglitazone to treat such medical disorders has gained significant interest, as it is believed that they may provide additional therapeutic efficacy and reduce the rate and severity of side effects compared to pioglitazone. Deuterated enantiopure pioglitazone has the potential to address these needs as it has been previously shown that incorporation of deuterium at the chiral center of pioglitazone stabilizes the enantiomers against inversion of configuration through a deuterium kinetic isotope effect. Deuterated enantiopure pioglitazone may also provide other related advantages. Thus, there is a need for useful methods for the synthesis of the deuterated enantiopure (R)-enantiomer and of the deuterated enantiopure (S)-enantiomer of pioglitazone.

SUMMARY OF THE INVENTION

One aspect of the invention provides a method of producing compound (IV), the method comprising the steps:

a) reacting compound (I) or salt thereof with D₂O and DCl at a temperature from about 80° C. to about 100° C. to produce compound (II) or salt thereof

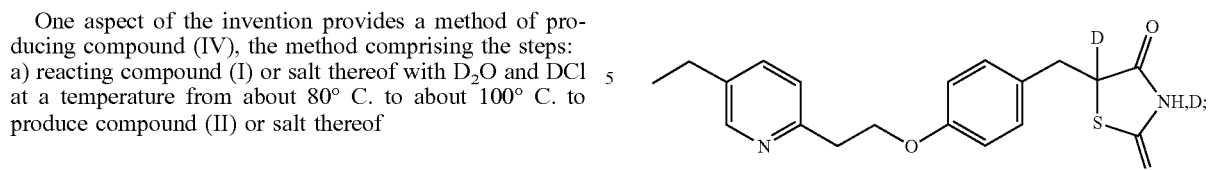

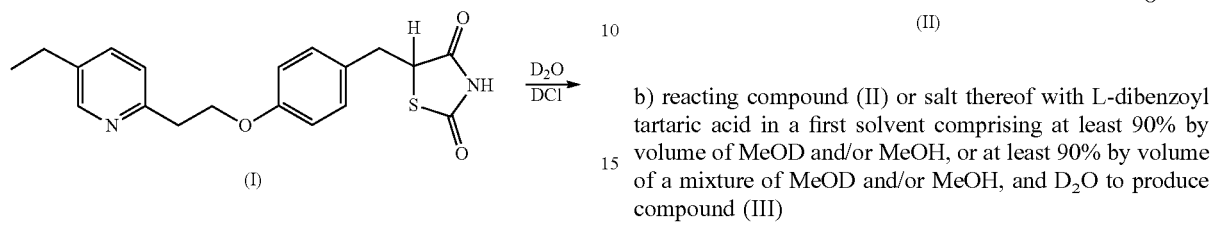

b) reacting compound (II) or salt thereof with L-dibenzoyl tartaric acid in a first solvent comprising at least 90% by volume of MeOD and/or MeOH, or at least 90% by volume of a mixture of MeOD and/or MeOH, and D₂O to produce compound (III)

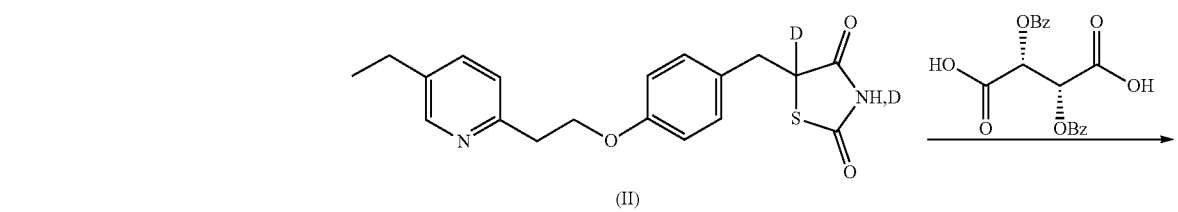

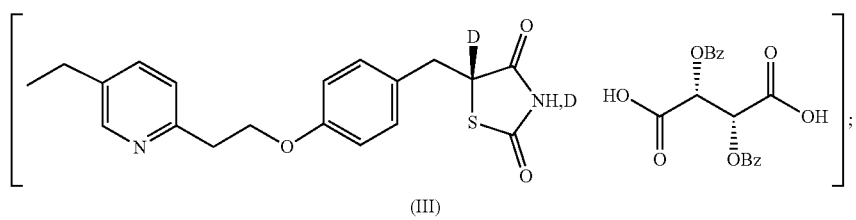

c) recrystallizing compound (III) one or more times in a second solvent comprising at least 90% by volume of a mixture of D₂O, DCl and/or HCl, and MeOH and/or MeOD to produce recrystallized compound (III')

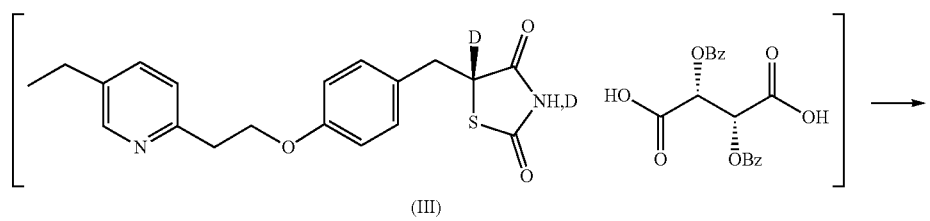

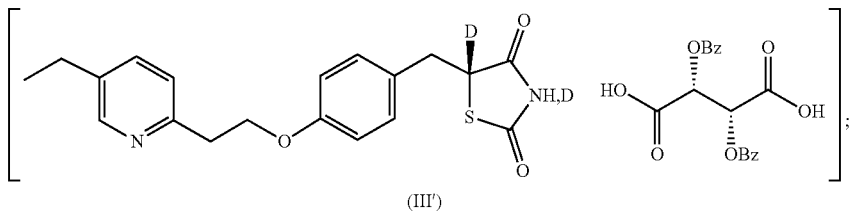

and d) reacting recrystallized compound (III') with DCl and/or HCl, in a third solvent which comprises deuterated and/or non-deuterated solvent, to produce compound (IV), or salt thereof, which is obtained by crystallization

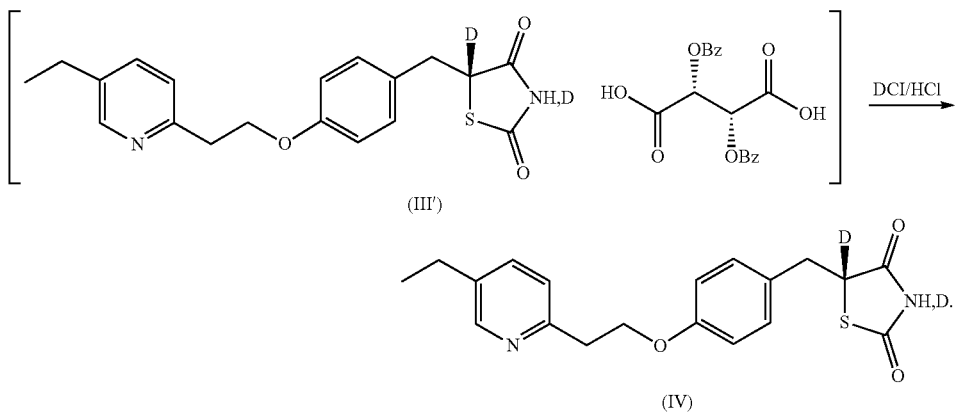

In another aspect, the invention provides compound (II) or salt thereof, and methods of synthesis thereof.

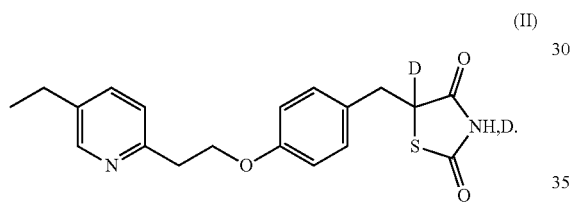

In another aspect, the invention provides compound (III'), and methods of synthesis thereof.

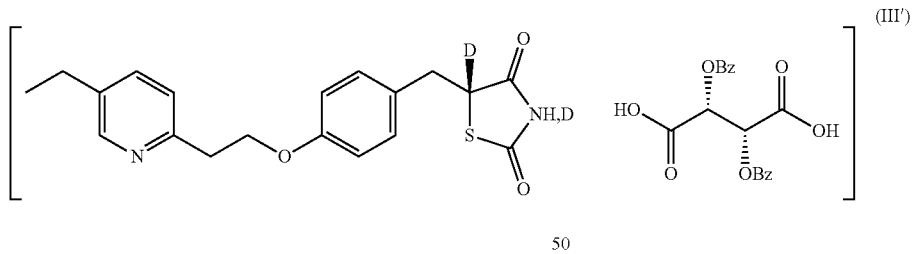

DETAILED DESCRIPTION

Figure 1A:
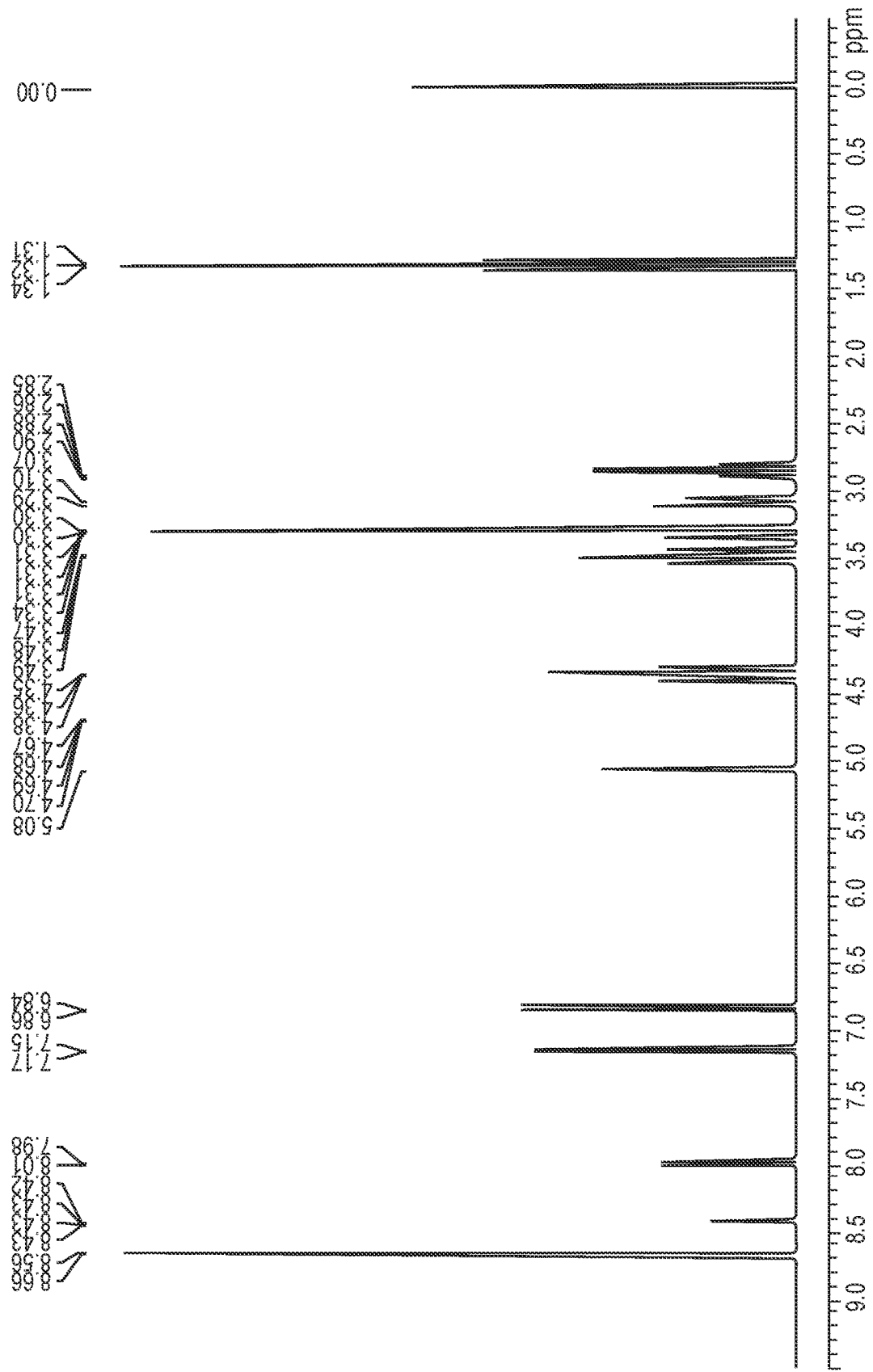
FIG. 1A depicts a $^1$H-NMR spectrum of compound (II) in DMSO-d6.

The disclosure provides methods of synthesis of enantiopure deuterium-enriched pioglitazone. Also provided are intermediates useful in the synthesis of deuterium-enriched pioglitazone and methods of synthesis of those intermediates. Deuterium enriched refers to the feature that the compound has a quantity of deuterium that is greater than in naturally occurring compounds or synthetic compounds prepared from substrates having the naturally occurring distribution of isotopes. The threshold amount of deuterium enrichment is specified in certain instances in this disclosure, and all percentages given for the amount of deuterium present are mole percentages.

The invention provides methods of synthesis of deuterium enriched (R)-pioglitazone, also referred to herein as compound (IV) shown below:

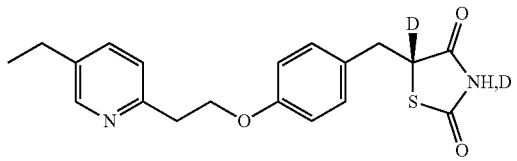

(IV)

or a pharmaceutically acceptable salt thereof.

The thiazolidinedione nitrogen in compounds (I) to (IV) can be bound to an H or a D or a combination of H and D, and may be depicted as "NH,D" to cover all of these possibilities. Any of compounds (I) to (IV) can be a salt, for example an HCl or DCl salt, or a combination of HCl and DCl salts.

Deuterium ($^2$H) is a stable, non-radioactive isotope of hydrogen and has an atomic mass of 2.014 u. Hydrogen naturally occurs as a mixture of the isotopes protium ($^1$H), deuterium ($^2$H), and tritium (3H). The natural abundance of deuterium is 0.015%. One of ordinary skill in the art recognizes that in all chemical compounds with an H atom, the H atom actually represents a mixture of protium ($^1$H), deuterium ($^2$H), and tritium (3H), where about 0.015% is deuterium. Thus, compounds with a level of deuterium that has been enriched to be greater than its natural abundance of 0.015% are considered unnatural and, as a result, novel over their non-enriched counterparts.

The deuterium-enriched pioglitazone described herein contains deuterium enrichment at the chiral center of pioglitazone and optionally in other locations in the compound. Deuterium-enrichment at the chiral center reduces the rate at which the two enantiomers of pioglitazone may interconvert. Further, the deuterium-enriched pioglitazone described herein is provided in enantiomerically pure form. This enantiomerically pure, deuterium-enriched pioglitazone provides for a better therapeutic agent than non-deuterated pioglitazone and/or mixtures of the compound and its mirror image.

The effects of deuterium modification on a compound's metabolic properties are not predictable, even when deuterium atoms are incorporated at known sites of metabolism. Only by actually preparing and testing a deuterated compound can one determine if and how the rate of metabolism will differ from that of its non-deuterated counterpart. See, for example, Fukuto et al. (J. Med. Chem. 1991, 34, 2871-76). Many compounds have multiple sites where metabolism is possible. The site(s) where deuterium substitution is required and the extent of deuteration necessary to see an effect on metabolism, if any, will be different for each compound. Deuteration at a chemically labile chiral center may result in stabilization against inversion of configuration. However, the magnitude of the effect is unpredictable. It is only by preparing the compound that the effect of deuterium can be ascertained.

I. Deuterium-Enriched Pioglitazone

One aspect of the invention provides a method of synthesis of deuterium-enriched compounds for use in the therapeutic methods and pharmaceutical compositions described herein. The deuterium-enriched compounds are provided in high enantiomeric purity in order to maximize therapeutic benefit, such as maximal potency per dose of therapeutic agent, and to minimize adverse side effects.

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, to 100% by weight.

Another aspect of the invention provides a unit quantum of a deuterium-enriched compound described herein, such as an amount of at least (a) one g, (b) one mg, or (c) one gram of a disclosed deuterium-enriched compound. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab/pilot scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical.

Industrial/commercial scale refers to the amount of product that would be produced in a batch that was designed for clinical testing, formulation, sale/distribution to the public, etc.

II. Methods of Synthesis

One aspect of the invention provides a method of producing compound (IV), the method comprising the steps:
a) reacting compound (I) or salt thereof with $D_2O$ and DCl at a temperature from about 80° C. to about 100° C. to produce compound (II) or salt thereof

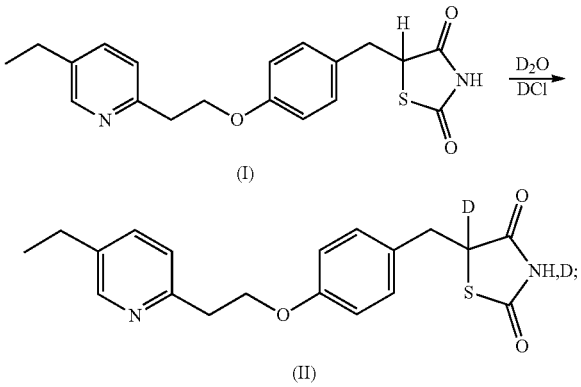

b) reacting compound (II) or salt thereof with L-dibenzoyl tartaric acid in a first solvent comprising at least 90% by volume of MeOD and/or MeOH, or at least 90% by volume of a mixture of MeOD and/or MeOH, and $D_2O$ to produce compound (III)

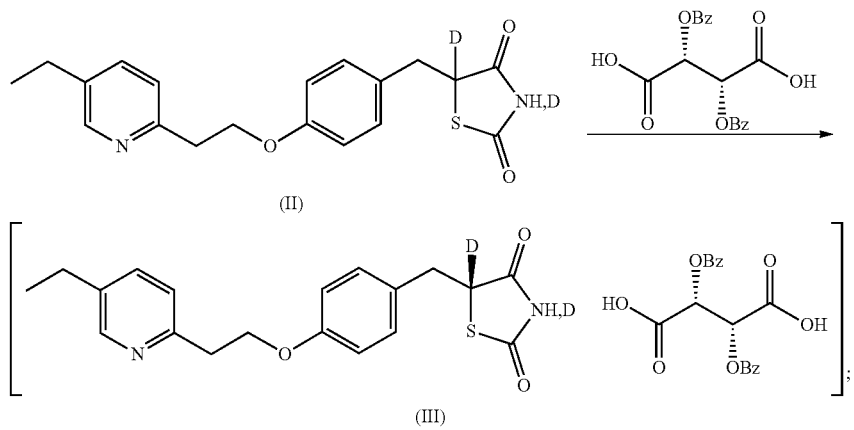

c) recrystallizing compound (III) one or more times in a second solvent comprising at least 90% by volume of a mixture of D₂O, DCl and/or HCl, and MeOH and/or MeOD to produce recrystallized compound (III')

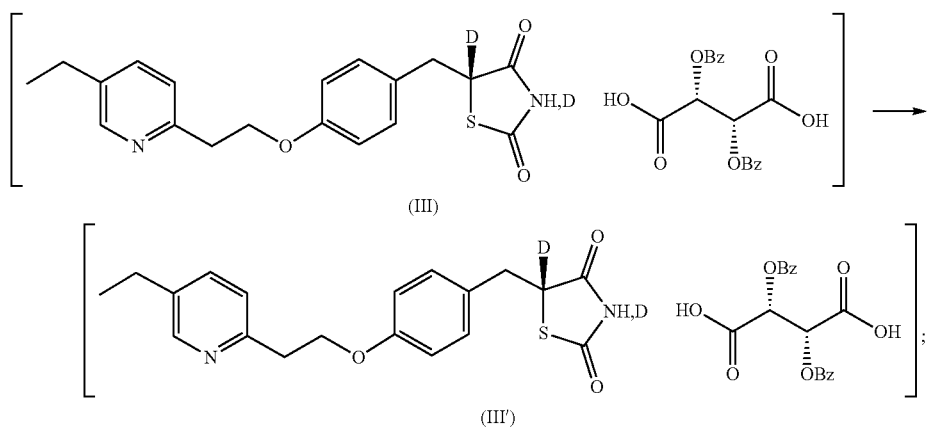

and
d) reacting recrystallized compound (III') with DCl and/or HCl, in a third solvent which comprises deuterated and/or non-deuterated solvent, to produce compound (IV), or salt thereof, which is obtained by crystallization

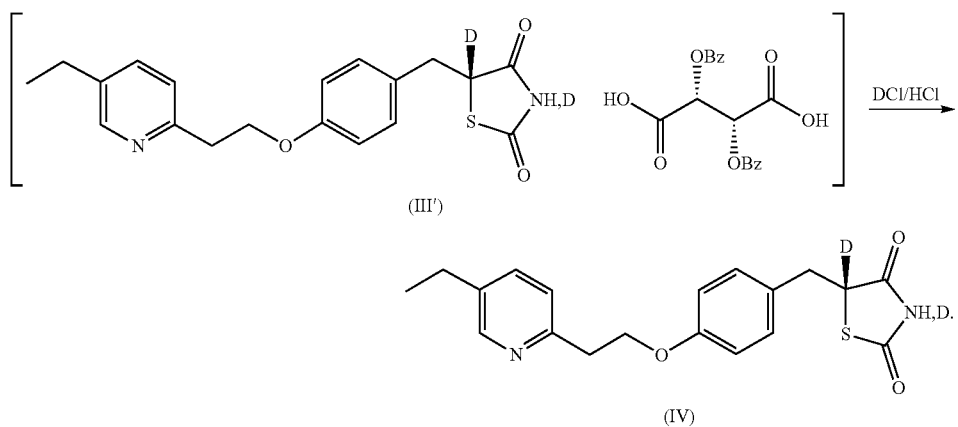

In some embodiments, the method comprises the steps:

a) reacting compound (I) HCl salt with D$_2$O and DCl at a temperature from about 80° C. to about 100° C. to produce compound (II) DCl salt.

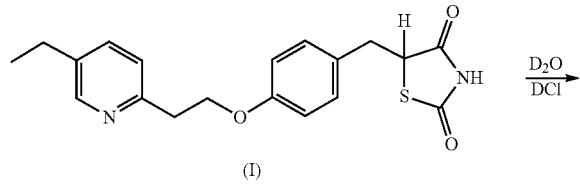

(I)

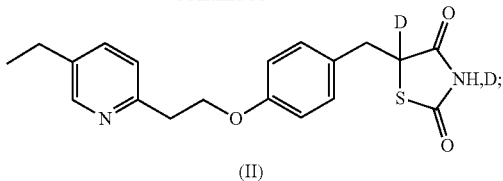

(II)

b) reacting compound (II) DCl salt with L-dibenzoyl tartaric acid in a first solvent comprising at least 90% by volume of MeOD and/or MeOH, or at least 90% by volume of a mixture of MeOD and/or MeOH, and D$_2$O to produce compound (III)

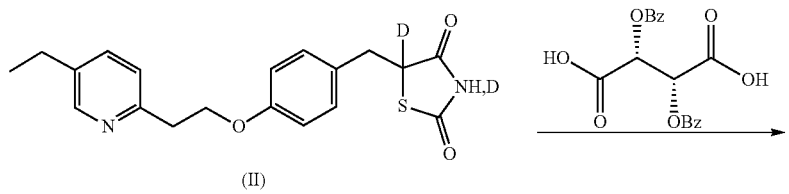

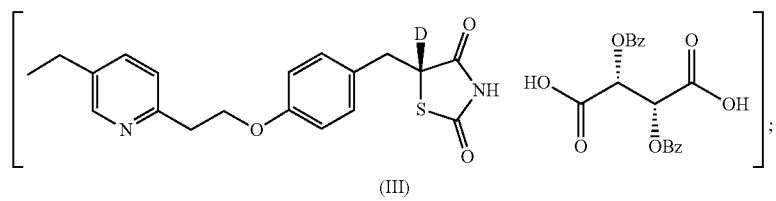

(III)

c) recrystallizing compound (III) one or more times in a second solvent comprising at least 90% by volume of a mixture of D$_2$O, DCl and/or HCl, and MeOH and/or MeOD to produce recrystallized compound (III')

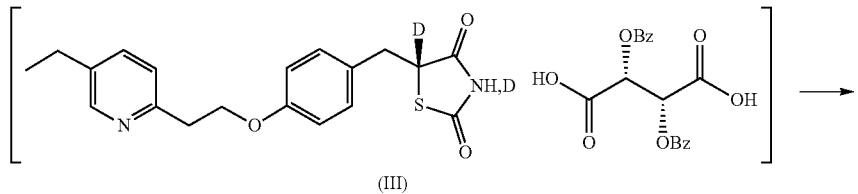

(III)

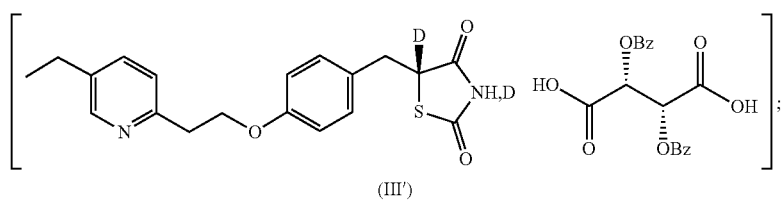

(III')

and d) reacting recrystallized compound (III') with DCl and/or HCl, in a third solvent which comprises deuterated and/or non-deuterated solvent, to produce compound (IV) DCl or HCl salt, which is obtained by crystallization

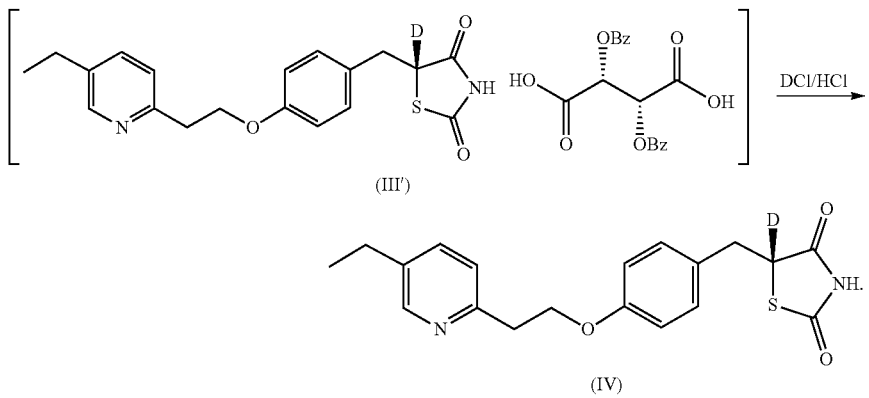

In some embodiments, step a) is carried out at a temperature from about 90° C. to about 100° C.

In some embodiments, step a) is repeated in multiple cycles.

In some embodiments, in step a) a mother liquor from a second or subsequent cycle is resubjected to the step a) conditions to obtain additional compound (II).

In some embodiments, the volume of D$_2$O in step a) is from about 3 to about 8 volumes w/w based on the weight of compound (I).

In some embodiments, step a) further comprises toluene, wherein the ratio of D$_2$O to toluene is from 1:3 to 3:1 by volume.

In some embodiments, in step b) the molar amount of L-dibenzoyl tartaric acid is from about 0.6 to about 3 molar equivalents based on the molar amount of compound (II). In some embodiments, in step b) the molar amount of L-dibenzoyl tartaric acid is from about 0.6 to about 1 equivalent based on the molar amount of compound (II).

In some embodiments, in step b) the first solvent is a mixture of D$_2$O and MeOD in a D$_2$O/MeOD ratio of from about 1:3 to about 3:1 by volume. In some embodiments, in step b) the first solvent is a mixture of D$_2$O and MeOD in a D$_2$O/MeOD ratio of from about 1.1:1 to about 1.2:1 by volume. In some embodiments, in step b) the first solvent D$_2$O/MeOD ratio is about 1.1:1 by volume.

In some embodiments, in step c) compound (III) is recrystallized once.

In some embodiments, in step c) the ratio of MeOH to MeOD is at least 95:5 by volume. In some embodiments, in step c) the ratio of MeOH to MeOD is no more than 5:95 by volume. In some embodiments, in step c) the ratio of MeOH to MeOD is from about 1:3 to about 3:1 by volume. In some embodiments, in step c) the ratio of MeOH to MeOD is from about 1:1.2 to about 1.2:1 by volume. In some embodiments, in step c) the ratio of MeOH to MeOD is about 1:1 by volume. In some embodiments, in step c) the ratio of MeOH to MeOD is about 7:3 by volume. In some embodiments, in step c) the second solvent D$_2$O:(MeOD+MeOH) ratio is about 1:1 by volume.

In some embodiments, in step c) the second solvent D$_2$O amount is from about 5 volumes w/w to about 10 volumes w/w and the (MeOD+MeOH) amount is from about 5 volumes w/w to about 10 volumes w/w based on compound (III).

In some embodiments, step c) is repeated in multiple cycles.

In some embodiments, in step d) compound (IV) or salt thereof is recrystallized.

In some embodiments, in step d) the third solvent comprises MeOH and/or MeOD. In some embodiments, in step d) the third solvent comprises no more than 20% by volume deuterated solvent. In some embodiments, in step d) the third solvent amount is from about 5 volumes to about 10 volumes w/w based on compound (III'). In some embodiments, in step d) the third solvent comprises at least 90% by volume a mixture of a deuterated or non-deuterated hydroxylic solvent and a non-deuterated-non-hydroxylic solvent. In some embodiments, the non-deuterated hydroxylic solvent is MeOH and the non-deuterated-non-hydroxylic solvent is ethyl acetate.

In some embodiments, in step d) compound (IV) is the HCl salt. In some embodiments, in step d) compound (IV) is the DCl salt.

In some embodiments, compound (IV) or salt thereof has at least 90% H attached to the thiazolidinedione nitrogen. In some embodiments, compound (IV) or salt thereof has at least 90% deuterium attached to the thiazolidinedione nitrogen.

In some embodiments, the enantiomeric excess of compound (IV) or salt thereof is at least 95%, at least 96%, at least 97%, at least 98%, or at least 99%.

In some embodiments, the HPLC purity of compound (IV) or salt thereof is at least 91%, at least 95%, at least 96%, at least 97%, at least 98%, at least 99%, at least 99.5%, or at least 99.8%.

In some embodiments, the deuterium content at the chiral center of compound (IV) or salt thereof is at least 90%, at least 93%, at least 95%, at least 96%, at least 97%, at least 98%, or at least 99%.

In some embodiments, for compound (IV) or salt thereof the enantiomeric excess is at least 96%, wherein the deuterium content at the chiral center is at least 96%, and the HPLC purity is at least 98%.

In another aspect, the invention provides compound (II) or salt thereof

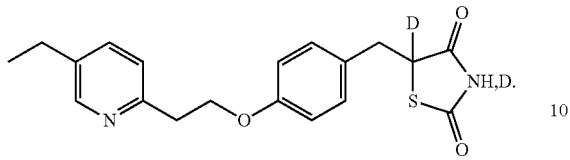

(II)

In another aspect, the invention provides a synthesis of compound (II) or salt thereof as described for step a) above and various embodiments.

In some embodiments of either the compound or synthesis, compound (II) or salt thereof has an HPLC purity of at least 98% or at least 99%.

In some embodiments of either the compound or synthesis, compound (II) or salt thereof has a deuterium content at the chiral center of at least 98% or at least 99%.

In another aspect, the invention provides compound (III')

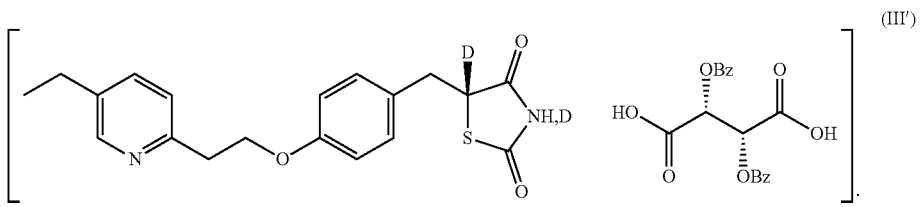

(III')

In another aspect, the invention provides a synthesis of compound (III') as described for steps a), b), and c) above and various embodiments.

In some embodiments of either the compound or synthesis, compound (III') has an HPLC purity of at least 98% or at least 99%.

In some embodiments of either the compound or synthesis, compound (III') has a deuterium content at the chiral center of at least 96% or at least 98%.

In some embodiments of either the compound or synthesis, compound (III') has a % de of at least 90% or at least 95%.

It should be noted throughout the application that compound (III) and compound (III') have the same chemical structure, but (III') is a recrystallized version of (III).

It should also be noted that the synthetic steps described herein can be used to prepare the (S)-enantiomer by using D-dibenzoyl tartaric acid in step b).

III. Pharmaceutical Compositions

The compounds of the disclosure can be used as a pharmaceutical composition comprising a compound described herein or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

In certain embodiments, the pharmaceutical composition comprises an effective amount of the active ingredient. In certain embodiments, the pharmaceutical composition comprises a therapeutically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

IV. Methods of Use

The compounds of the disclosure can be used in methods to treat medical disorders. Preferred medical disorders for treatment include metabolic disorders, neurological disorders, cancer, inflammatory disorders, respiratory disorders, bacterial infections, and fungal infections. Use of deuterium-enriched compounds having high enantiomeric purity is contemplated to maximize therapeutic benefits, such as achieving increased potency per dose of therapeutic agent and minimize adverse side effects.

Accordingly, the compounds of the disclosure can be used in a method of treating a medical disorder in a patient. The method comprises administering to a patient in need thereof a therapeutically effective amount of a compound described herein, such as a deuterium-enriched compound described herein, to treat the disorder. In certain embodiments, the compound is administered orally. Exemplary medical disorders for treatment are described in more detail below.

Another use for the compounds of the disclosure is in a method of treating a medical disorder in a patient. The method comprises orally administering to a patient in need thereof a therapeutically effective amount of a compound of the disclosure to treat the disorder. Exemplary medical disorders for treatment are described in more detail below. For example, the use may be for treating non-alcoholic steatohepatitis (NASH), adrenoleukodystrophy (ALD), or adrenomyeloneuropathy (AMN). Another use for the compounds of the disclosure is in a method of inducing death of a bacterial cell. The method comprises exposing a bacterial cell to an effective amount of a deuterium-enriched compound described herein to induce death of said bacterial cell. In certain embodiments, the method comprises inducing death of a population of bacterial cells.

Another use for the compounds of the disclosure is in a method of inducing death of a fungus. The method comprises exposing a fungus to an effective amount of a deuterium-enriched compound described herein to induce death of said fungus. In certain embodiments, the method comprises inducing death of a population of fungi.

Metabolic Disorders

In some cases, the compounds of the disclosure may be useful to treat a metabolic disorder. Exemplary metabolic disorders include, for example, diabetes (e.g., type I diabetes and type II diabetes), nonalcoholic steatohepatitis, non-alcoholic fatty liver disease, viral hepatitis, liver cirrhosis, liver fibrosis, diabetic retinopathy, diabetic neuropathy, diabetic nephropathy, beta cell depletion, insulin resistance in a patient with congenital adrenal hyperplasia treated with a glucocorticoid, dysmetabolism in peritoneal dialysis patients, reduced insulin secretion, improper distribution of brown fat cells and white fat cells, obesity, and improper modulation of leptin levels. In certain embodiments, the metabolic disorder is further selected from a complication of diabetes. In some cases, the metabolic disorder is type I diabetes, non-alcoholic fatty liver disease, viral hepatitis, liver cirrhosis, liver fibrosis, diabetic retinopathy, diabetic neuropathy, diabetic nephropathy, beta cell depletion, insulin resistance in a patient with congenital adrenal hyperplasia treated with a glucocorticoid, dysmetabolism in peritoneal dialysis patients, reduced insulin secretion, improper distribution of brown fat cells and white fat cells, obesity, or improper modulation of leptin levels. In some cases, the metabolic disorder is non-alcoholic fatty liver disease, diabetic retinopathy, diabetic neuropathy, diabetic nephropathy, beta cell depletion, or insulin resistance in a patient with congenital adrenal hyperplasia treated with a glucocorticoid. In some cases, the metabolic disorder is non-alcoholic fatty liver disease, diabetic retinopathy, diabetic neuropathy, diabetic nephropathy, beta cell depletion, reduced insulin secretion, improper distribution of brown fat cells and white fat cells, obesity, or improper modulation of leptin levels. In some cases, the metabolic disorder is non-alcoholic fatty liver disease. In some cases, the metabolic disorder is beta cell loss treatable by beta-cell regeneration. In some cases, the metabolic disorder is central obesity, dyslipidemia, or pre-diabetes.

V. Definitions

To facilitate an understanding of the present invention, a number of terms and phrases are defined below.

The term "compound" refers to a quantity of molecules that is sufficient to be weighed, tested for its structural identity, and to have a demonstrable use (e.g., a quantity that can be shown to be active in an assay, an in vitro test, or an in vivo test, or a quantity that can be administered to a patient and provide a therapeutic benefit).

Unless otherwise stated, when a position is designated specifically as "H" or "hydrogen," the position is understood to have hydrogen at its natural abundance isotopic composition. Also, unless otherwise stated, when a position is designated specifically as "D" or "deuterium," the position is understood to have deuterium (i.e., $^2H$) at an abundance that is at least 80%.

The term "isotopic enrichment factor" as used herein means the ratio between the isotopic abundance of deuterium at the specified position in a compound of this invention and the naturally occurring abundance of that isotope.

Increasing the amount of deuterium present in a compound is called "deuterium-enrichment," and such compounds are referred to as "deuterium-enriched" compounds. If not specifically noted, the percentage of enrichment, "deuterium grade," or deuterium content refers to the percentage of deuterium present in the compound at a particular atom. The deuterium grade is determined by $^1H$-NMR analysis in DMSO-d6 or MeOD.

"Total deuterium count", which is the total number of deuteriums in the average molecule, is measured by deuterium NMR.

Because the natural abundance of deuterium is about 0.015%, approximately one in every 6,667 naturally occurring sites of hydrogen in a compound described herein would be expected to have a deuterium present.

All percentages given for the amount of deuterium present are mole percentages.

It can be difficult in the laboratory to achieve 100% deuteration at any one site of a lab scale amount of compound (e.g., milligram or greater). When 100% deuteration is recited it is assumed that a small percentage of hydrogen may still be present. Deuterium enrichment can be achieved by either exchanging protons with deuterium or by synthesizing the molecule with enriched starting materials.

Also described herein is the isolation or purification of deuterium-enriched compounds of structures (I) to (IV).

Isomers, e.g., stereoisomers, can be isolated from mixtures by methods known to those skilled in the art, including chiral high-performance liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, N Y, 1962); and Wilen, Tables of Resolving Agents and Optical Resolutions p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

The term "enantiomeric excess" is defined as the fraction of a chiral substance that is a single enantiomer in excess of the fraction that is racemic. For example, the % enantiomeric excess ("% ee") for a major R enantiomer in an R/S mixture is calculated by the formula:

% ee of R enantiomer=100%×[(amount of R)−(amount of S)]/(amount of R+amount of S)

Similarly, for the term "diastereomeric excess" the % diastereomeric excess ("% de") for a major diastereomer A in an A/B mixture is calculated by the formula:

% de of A diastereomer=100%×[(amount of A)−(amount of B)]/(amount of A+amount of B)

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The term "diastereomerically pure" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of a single diastereomer. Methods for determining diastereomeric and enantiomeric purity are well-known in the art. Diastereomeric purity can be determined by any analytical method capable of quantitatively distinguishing between a compound and its diastereomers, such as high-performance liquid chromatography (HPLC) or NMR $^1$H.

The term "RRT" is "relative retention time," and is used herein to compare the retention time of a secondary peak compared to the main peak of a chromatographic separation or analysis. It is primarily used herein to identify peaks corresponding to impurities.

The articles "a" and "an" may be used herein to refer to one or to more than one (i.e. at least one) of the grammatical objects of the article. By way of example "an analogue" means one analogue or more than one analogue.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., J. Pharm. Sci. (1977) 66(1): 1-79.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the subject.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances, the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture" or "racemate."

"Tautomers" refer to compounds that are interchangeable forms of a particular compound structure, and that vary in the displacement of hydrogen atoms and electrons. Thus, two structures may be in equilibrium through the movement of J electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition.

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, if a variable is not accompanied by a definition, then the previous definition of the variable controls.

Finally, the invention may be embodied in other specific forms without departing from the spirit or essential attributes thereof. This invention encompasses all combinations of aspects and embodiments of the invention noted herein. It is understood that any and all aspects of the invention may be taken in conjunction with any other aspects and/or embodiments to describe additional aspects. It is also to be understood that each individual element of the aspects is intended to be taken individually as its own independent aspect. Furthermore, any element of an aspect is meant to be combined with any and all other elements from any aspect to describe an additional aspect.

EXAMPLES

The invention, now being generally described, will be more readily understood by reference to the following examples, which are included merely for purposes of illustration of certain aspects and embodiments of the present invention, and are not intended to limit the invention.

Reaction temperatures are reported as internal temperatures. Chemical intermediates, reagents, and solvents were obtained from commercial sources.

Filtration: Solid products were isolated by filtration over a PTFE Buchner funnel using MN 617 G (fast filtration, phosphate-free; ref: MN 494024) and MN640m (ref: MN 203015) filter paper (unless otherwise stated) and washed with 1:1 MeOD:$D_2O$ (v/v) in a plug-flow method (portions; 2×/3×) (unless otherwise stated).

Drying: After filtration, first solids were air-dried in vacuo for a few hours (3-4 h) and then dried (24-72 h) in a drying oven at 50° C./42° C. fitted with a vacuum pump.

NMR: $^1$H spectra were recorded on a Bruker Avance 300 MHz or higher spectrometer. Chemical shifts were referenced to residual solvent signals at δ 2.50 (DMSO-d6) relative to TMS as internal standard wherever applied.

HPLC: For % d.e./% e.e. measurement, all samples were dissolved in MeOD to make a solution of 1 mg/mL.

HPLC for identity and chemical purity measurement: Samples were run on a 150 mm×4.6 mm, 5 μm YMC triart C18 column. The mobile phase was an isocratic elution system with 1:1 0.1 M $NH_4OAc$:$CH_3CN$ plus 2% HOAc. Flow rate was 0.75 mL/min; run time, 35 min; and detector wavelength, 269 nm.

In the following examples, when details of an example run are presented, notes in square brackets ([ ]) are used to denote optional changes that are not part of the example run but could be performed or were performed in another run.

Example 1—Preparation of Racemic Deuterated Pioglitazone, (Compound (II))

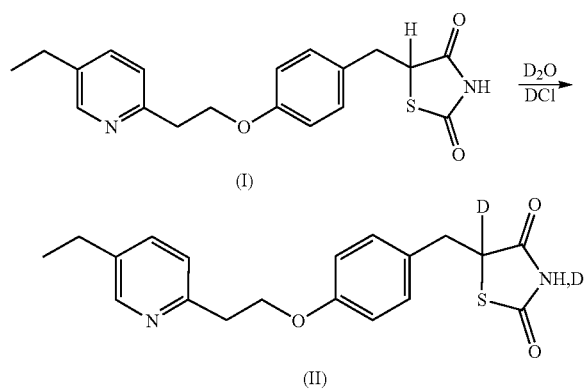

Pioglitazone-HCl (compound (I) HCl salt) was dissolved in D₂O at elevated temperature. After stirring at 90 to 100° C. for at least 5 h, a small amount of DCl was added followed by cooling down to room temperature. After aging the suspension for a few hours at 15 to 25° C., the product was filtered off as compound (II) DCl salt. After this first cycle, typically approximately 95% of the hydrogen at the chiral center had been exchanged by deuterium. If desired, the crude product was then subjected to a second cycle of the same treatment to further increase the deuteration grade to 98+% in compound (II) as determined by ¹H-NMR.

Example Run:

1ˢᵗ deuteration cycle: 19.96 kg pioglitazone (compound (I)) was charged in a 100 L glass-lined vessel. 79.54 kg (71.86 L; 4.0 equivalents w/w) D₂O was then charged in the same vessel. The reaction mixture was heated and stirred to about 95° C. and stirred at that temperature for 5 h. [Temperatures can be from about 90 to about 100° C. (preferably 95° C.) for at least 5 h. A temperature of 95° C. or lower will lead to lower deuteration grade, while temperatures from about 95 to about 100° C. worked better. Lower amounts of D₂O were tried, but the reaction mixture was difficult to stir with less than 4 w/w equivalents, and increase in deuteration was minimal above 5 w/w equivalents. Significant increase in deuteration grade was observed up until 3 to 4 hours at elevated temperature.] A thin white suspension was observed and 0.13 kg (0.10 L, 0.005 v/w equivalents) 35% DCl in D₂O was added, and the transfer line was rinsed with approximately 0.25 L D₂O (0.0125 v/w equivalents). The reaction mixture was cooled to about 25° C. over 240 min approximately [Cooling time is at least 3 h to a final temperature from about 15 to about 25° C.]. The reaction mixture was then stirred for 13 h approximately at 15° C. [Holding time is at least 5 h from about 15 to about 25° C. The solid obtained is more stirrable and filterable if cooled over 3 hours or more rather than only 1 hour.] The crude product was filtered off on a 140 L stainless steel nutsche filter. The product was washed with 5.52 kg (4.99 L; 0.25 v/w equivalents) D₂O. The crude product was blown dry in a stream of nitrogen for 3 h approximately [Drying time should be at least 1 h]. The moist crude product was isolated, and a monitoring sample was used for ¹H-NMR. The sample was then subjected to a second round of deuteration to increase the deuterium content. [Over three runs, % deuteration on chiral center of 96.5%, 97.2%, and 96.9% were observed at this stage.]

Figure 1B:
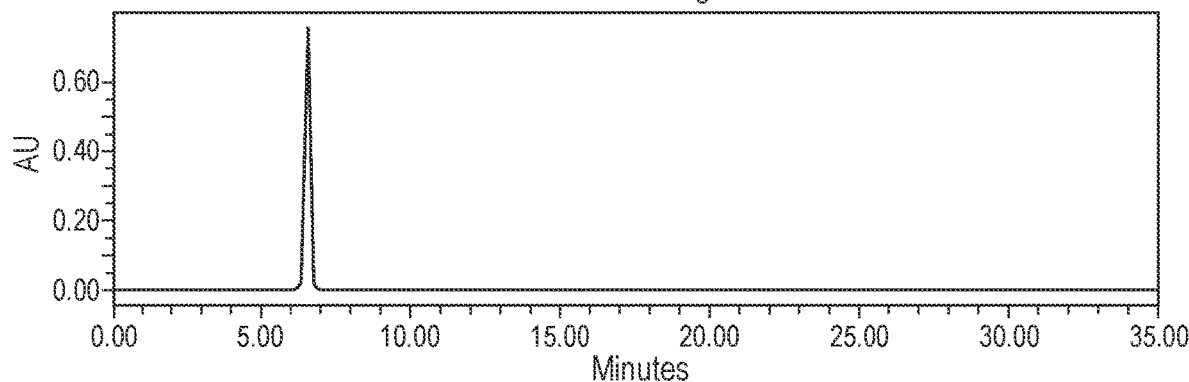
FIG. 1B depicts an LC trace showing chemical purity of compound (II)
Figure 1B:
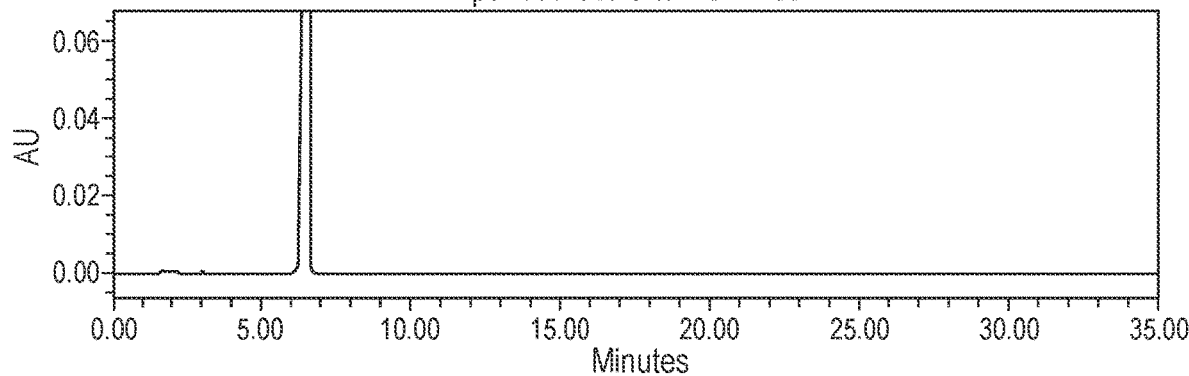

Second deuteration cycle: The entire amount of moist crude product was charged in a vessel. 75.57 kg (68.26 L) D₂O was then charged. The reaction mixture was heated to about 95° C. for 5 h approximately [Heating can be to a temperature from about 90 to about 100° C. (preferably 95° C.) for at least 5 h]. A thin white suspension was observed. 0.12 kg (0.09 L) DCl in D₂O 35% was then added, and the transfer line was rinsed with approximately 0.25 L D₂O. The reaction mixture was cooled to 25° C. over 4 h [Cooling ramp should be at least 3 h to a temperature from about 15 to about 25° C.]. The reaction mixture was stirred at about 20° C. for 9 h [Stirring can be done at 15 to 25° C. for at least 5 h]. Then the crude product was filtered off on a 140 L stainless steel nutsche filter and was rinsed with 5.52 kg (4.99 L) D₂O. Deuterium NMR showed more than 2 deuteriums per molecule. The compound (II) DCl salt product (or optionally a mixture of HCl and DCl salt) was dried on a 140 L stainless steel nutsche filter in vacuo at about max. 60° C. until LOD (loss on drying)<2% (48 h approximately) [Drying temperature should not exceed a maximum of 60° C.]. Example analysis data for run K-2 can be found in FIGS. 1A and 1B.

Optional Re-Use of Mother Liquor from a Second Deuteration Cycle for a First Deuteration Cycle:

A suspension of 1.425 kg (3.627 mol) of (I) and 7.125 kg or 6.5 L (355.76 mol, 5 eq. w/w) D₂O (5.7 L mother liquor from a second deuteration cycle and 0.8 L fresh D₂O) was heated at 100° C. (at 70° C. a clear solution was obtained) and stirred at this temperature for 5 hours. No DCl in D₂O was added to the mixture (since the mother liquor contained residual DCl+HCl). The reaction mixture was allowed to attain ambient temperature (21° C.) over 8 h and was stirred at this temperature for 7 h. The precipitated (II) DCl salt was collected by filtration to give a wet cake. After drying in vacuo at 50° C. for 72 h, in total, 1.408 kg of (II) DCl salt was obtained (Yield=98.3%) as an off-white solid. ¹H-NMR (300 MHz) analysis revealed 91.6 atom % D at the chiral center.

A suspension of the above 1.408 kg of (II) DCl salt and 7.04 kg (351.51 mol, 5 eq. w/w) fresh D₂O was heated to 100° C. and was stirred at this temperature for 5.5 hours. Subsequently, 35% DCl in D₂O (0.00704 L, ~0.015 eq.) was added to the mixture. The mixture was then allowed to cool to ambient temperature (21° C.) over 8 h and was stirred at this temperature for another 7 h. The precipitated DCl salt of compound (II) was collected by filtration to give a wet cake. After drying in vacuo at 50° C. for 72 h, 1.326 kg of (II)·DCl was obtained as an off-white solid (Yield=94.2%). ¹H-NMR (300 MHz) analysis revealed 99 atom % D at the chiral center.

| Kilo/pilot scale run Results: | | | | | |
|---|---|---|---|---|---|
| Entry | Input form. (I) (kg) | Input $D_2O$ (w/w) | Reaction Time (h) | Yield (%) | Chemical purity by HPLC (%) | D content at chiral center by $^1H$ NMR (%) |
| K-1 | 19.8 | 4 | 5 | 92 | 99.6 | 98.6 |
| K-2 | 20.0 | 4 | 5 | 94 | 99.8 | 99.4 |
| K-3 | 62.5 | 4 | 5 | 90 | 99.8 | 99.7 |

For entry K-1: Color white to off-white; Appearance solid; $^1$H-NMR consistent with structure, deuteration grade (by $^1$H-NMR) 99.7%; purity (% area by HPLC) 99.8%; impurities 0.10%, 0.07%; loss on drying 0.16%

| Laboratory scale runs with modifications: | | | | | | |
|---|---|---|---|---|---|---|
| Entry | Input form. (I) (g) | Input $D_2O$ (w$D_2O$/w(I) or w/w) | Reaction Time (h) | Yield (%) | Chemical purity by HPLC (%) | D content at chiral center by $^1H$ NMR (%) |
| 1 | 20 | 5 | 5 | 90 | 99.3 | 98.7 |
| 2 | 20 | 4 | 5 | 90 | 99.1 | 97.9 |
| 3 | 20 | 3 | 5 | 88 | 98.0 | 98.6 |
| 4 | 5 | 5 | 22 | 84 | 96.2 | 98.6 |
| 5 | 20 | 4 | 5 | 90 | 98.8 | 98.6 |
| 6 | 20 | 4 | 5 | 85 | 99.6 | 91.1 |
| 7 | 20 | 4 | 5 | 84 | 99.8 | 96.9 |
| 8 | 5 | 4 | 5 | 98 | 99.7 | 85.0 |
| 9 | 10 | 1(+5) | 5 | 89 | 99.5 | 96.7 |
| 10 | 10 | 1(+5) | 5 | 23 | 99.8 | 18 |
| 11 | 45 | 4 | 5 | 90 | 99.6 | 96.9 |
| 12 | 30 | 4 | 5 | 91 | 99.8 | 98.7 |
| 15 | 20 | 2(+2) | 5 | 94 | 99.8 | 98.8 |
| 16 | 20 | 4 | 5 | 91 | 99.9 | 99.7 |
| 17 | 20 | 2(+2) | 5 | 96 | 99.7 | 99.8 |
| 18 | 32 | 4 | 5 | 92 | 99.8 | 98.8 |
| 19 | 20 | 4 | 5 | 90 | 99.5 | 99.1 |

In entry 1, test under selected conditions afforded successful results (good yield and quality achieved).
In entry 2, lower amount of $D_2O$ was tested, 4 w/w instead of 5 w/w; reaction worked well; after addition of DCl and upon cooling suspension becomes quite thick, just about stirrable.
In entry 3, still lower amount of $D_2O$ was tested, 3 w/w instead of 5; reaction worked well; after addition of DCl & upon cooling suspension becomes very thick, not completely stirrable anymore.
In entry 4, a small experiment was performed and intentionally thermally stressed longer (overnight at 100° C.) to check impact on product quality.
In entry 5, the 4 w/w conditions of entry 2 were repeated, HPLC quality similar to entry 2, deuteration grade better/similar to entries 1 and 3.
In entry 6, the 4 w/w conditions were tested at 80° C. instead of 100° C.; in this way significantly lower deuteration grade but higher chemical purity were observed.
In entry 7, the 4 w/w conditions were tested at 90° C. instead of 100° C.; in this way slightly lower deuteration grade but higher chemical purity were observed.
In entry 8, the mother liquor of the second cycle of entry 7 was used instead of fresh $D_2O$ for the first cycle; due to DCl in mother liquor reaction mixture is a solution at elevated temperature.
In entry 9, only 1 volume w/w of $D_2O$ plus 5 w/w inert solvent (toluene) were tested; product crystallized out quite sticky with a lot of wall caking, not well stirrable and difficult to transfer onto filter; $2^{nd}$ cycle was performed, quite good purity and deuteration grade were reached.
In entry 10, only 1 w/w $D_2O$ with 5 w/w dioxane was tested, reaction mixture became a clear solution at ~50° C. already, after DCl addition and upon cooling it did not crystallize out right away, some second crop could be isolated but yield was still low; deuteration grade was very low.
In entry 11, the batch of DCl for kilolab run was use-tested.
In entry 12, the pioglitazone for kilolab run was use-tested.
In entry 15, another attempt of a co-solvent was made by using 2 w/w $D_2O$ with 2 w/w toluene; slightly better for stirrability then entry 9 but still not as good as pure $D_2O$.
In entry 16, the pioglitazone for the kilolab run and the second delivery of $D_2O$ were use-tested positively.
In entry 17, the conditions of entry 15 were repeated, stirrability observed was better.
In entry 18, pioglitazone planned for production were use-tested showing no issue.

Example 2—Preparation of Enantioenriched (R)-Deuterated Pioglitazone L-Dibenzoyl Tartrate Salt (Compound (III))

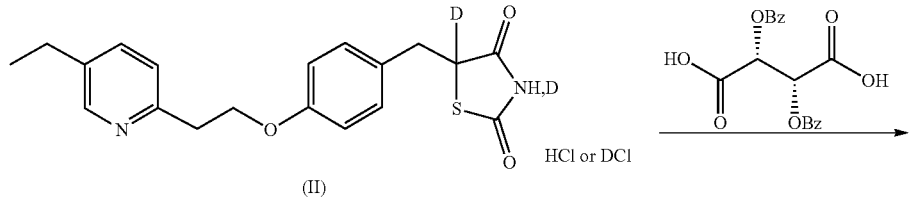

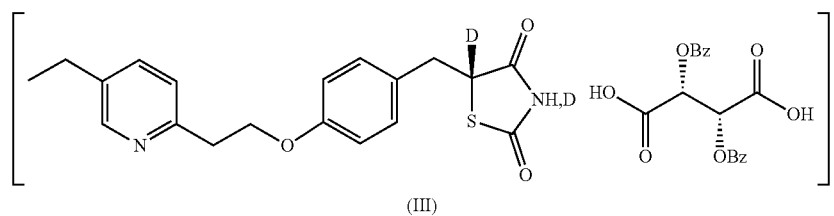

The synthesis started with dissolving compound (II) or salt thereof and L-dibenzoyl tartrate in a mixture of MeOD (methanol-dl) and D₂O at elevated temperature. The mixture was then cooled to approximately 55° C. Seed crystals (2% or less w/w relative to (II)) were optionally added, followed by a rather slow cooling ramp and extended aging time. Eventually, the product compound (III) was filtered off, washed with a mixture of MeOD and D₂O and dried in vacuo.

Example Run:

28.10 kg Racemic deuterated pioglitazone (compound (II)) DCl salt was charged in a 1000 L glass vessel, followed by 25.49 kg L,L-dibenzoyltartaric acid (1 molar equiv) and 187.3 kg MeOD (230.4 L; 6.67 w/w equivalents) [It is possible to use 0.6 molar equivalents of L,L-dibenzoyltartaric acid resulting in slightly lower yield but comparable % ee]. The reaction mixture was warmed to a temperature from about 60 to about 70° C. (65° C. achieved), and 280.9 kg D₂O (253.7 L; 10.0 w/w equivalents) was added. [A 1:1 v/v mixture of MeOD and MeOH can be used in place of MeOD, with resulting deuteration grade of 97.4% after first crystallization. MeOH only can also be used, with resulting deuteration grade of 94.4% after first crystallization]. The reaction was warmed to 70 to 80° C. (76° C. achieved), and the mixture was stirred at that temperature for at least 30 minutes. An almost clear solution was obtained. The mixture was then cooled to 55° C. over 66 min [Cooling time should be at least one hour to a temperature from about 52 to about 58° C.]. The mixture was then stirred for 2 h at 56° C. [Stirring can be done for at least 2 hours at a temperature from about 52 to about 58° C.]), during which time seed crystals (0.25 kg) of compound (III) were added [Seeding can be with crystals of compound (III) or (III')]. The suspension was cooled to 25° C. for 7.5 hours [Cooling time to a temperature from about 22 to about 28° C. should be at least 5 hours]. Then the suspension was stirred for 37 h [Stirring should take at least 15 hours at 22 to 28° C.]).

Figure 2A:
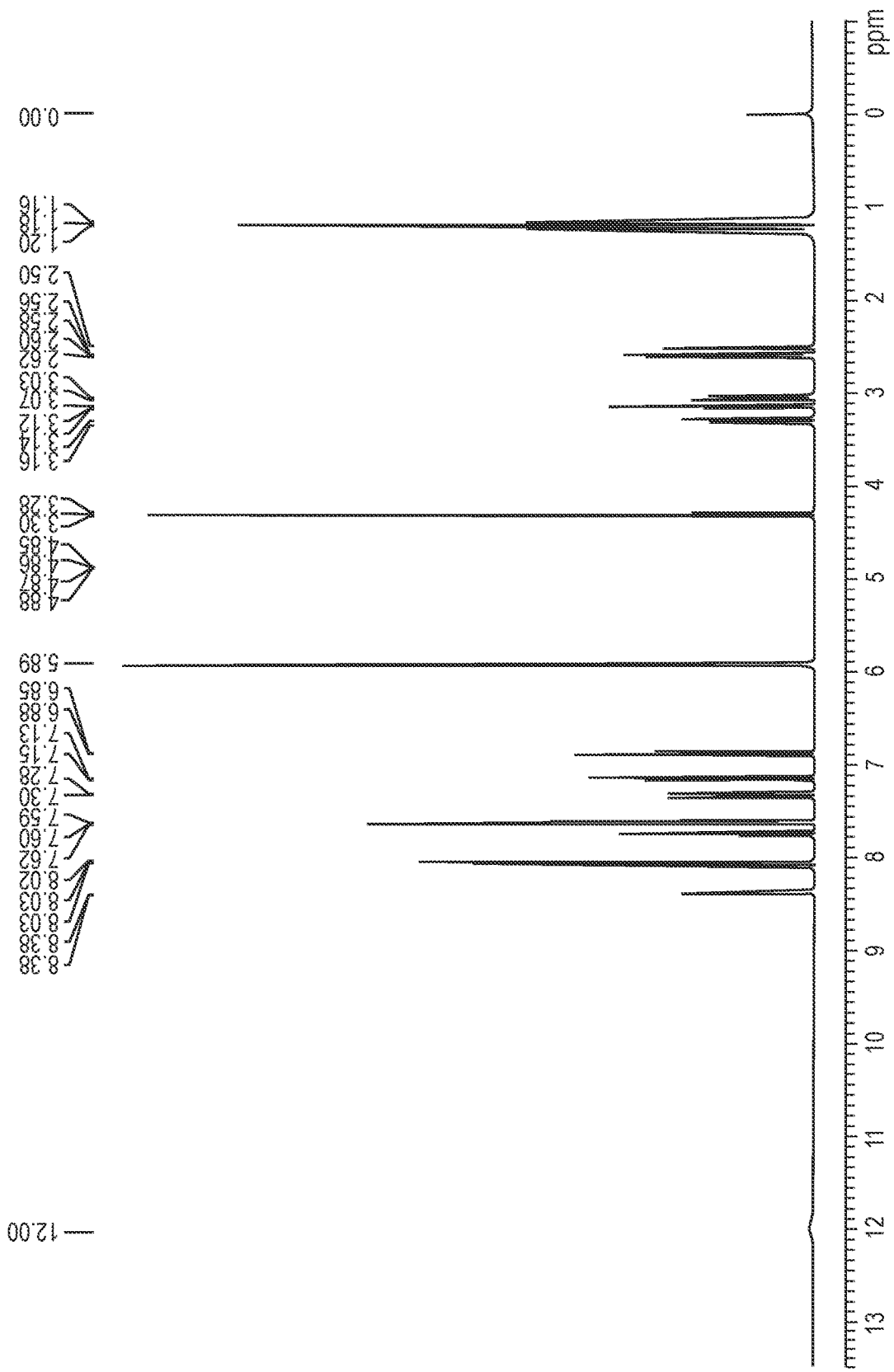
FIG. 2A depicts a $^1$H-NMR spectrum of compound (III) in DMSO-d6.
Figure 2B:
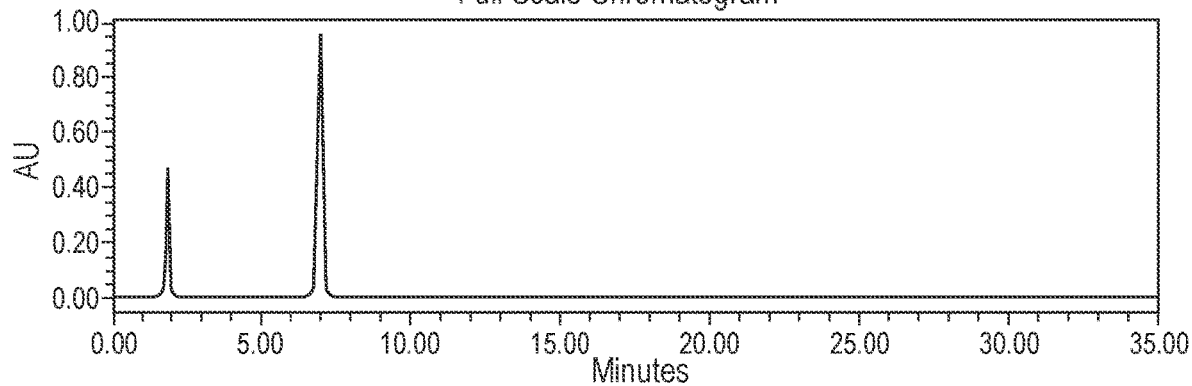
FIG. 2B depicts an LC trace showing chemical purity of compound (III)
Figure 2B:
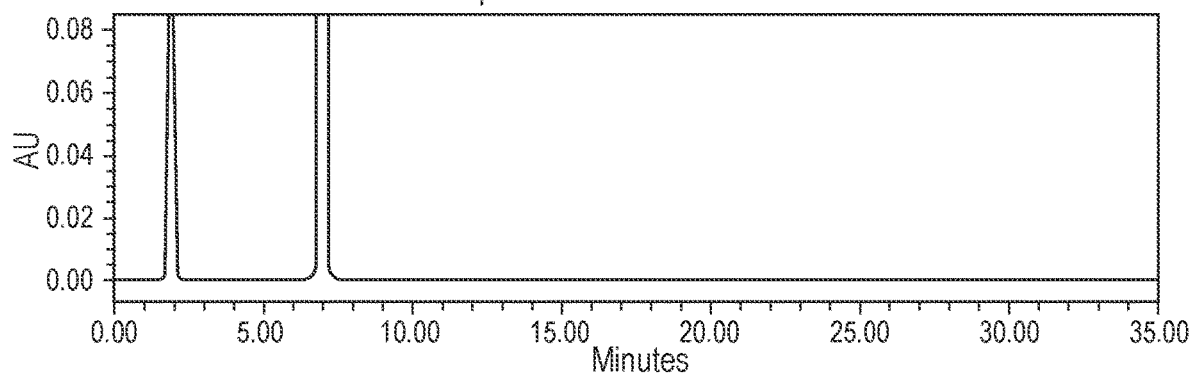
Figure 2C:
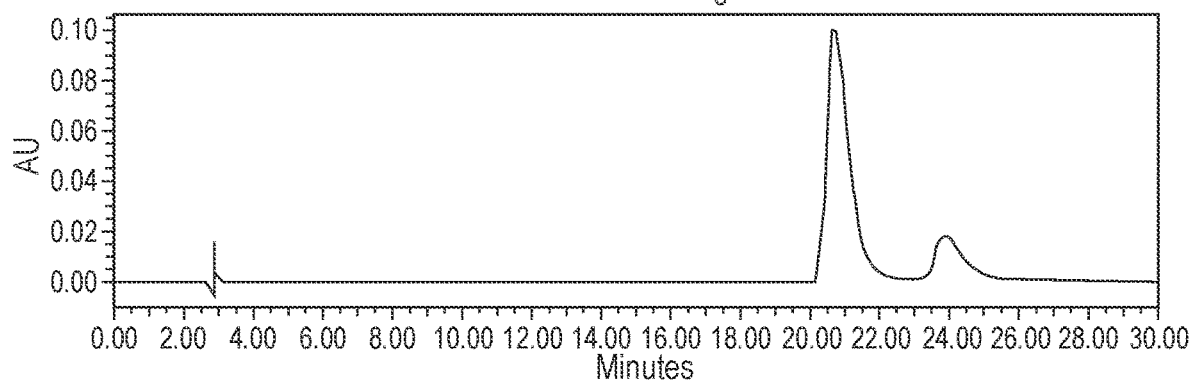
FIG. 2C depicts an LC trace showing optical purity of compound (III)
Figure 2C:
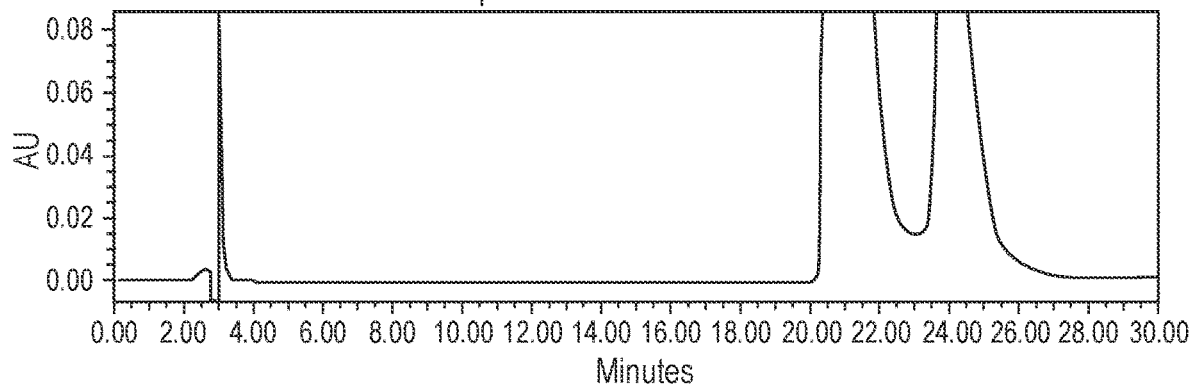

The product was filtered off on a stainless-steel centrifuge, and was washed with a premixed mixture of D₂O (13.38 kg; 12.08 L; 0.48 w/w equiv) and MeOD (9.82 kg; 12.08 L; 0.35 w/w equiv). The product was blown dry in a steam of nitrogen for at least 1 h. The product was then dried in vacuo at a maximum temperature of 60° C. on a Hastelloy vacuum tray dryer. Deuterium NMR showed approximately 2 deuteriums per molecule. Example analysis data can be found in FIGS. 2A, 2B, and 2C.

| | | | Kilo Scale runs | | | |
|---|---|---|---|---|---|---|
| Entry | Input of (II) (g) | Cool Ramp (° C.) | Yield of (III) final (%) | Chemical purity by HPLC (%) | % de by chiral HPLC (%) | D content at chiral center by ¹H NMR(%) |
| K-1 | 36.72 | 60→20 | 52.8 | 99.3 | 54.2 | 99.4 |
| K-2 | 28.10 | 55→25 | 47.0 | 99.9 | 64.1 | 99 |
| K-3 | 27.94 | 55→25 | 46.6 | 99.9 | 65.8 | 99 |

For K-2: Color white; Appearance solid; ¹H-NMR consistent with structure, deuteration grade (by ¹H-NMR) 99%; purity (% area by HPLC) 99.9%; no more than 0.05% impurities; loss on drying 0.39%

For K-3: Color white; Appearance solid; ¹H-NMR consistent with structure, deuteration grade (by ¹H-NMR) 99%; purity (% area by HPLC) 99.9%; no more than 0.05% impurities; loss on drying 0.45%

Laboratory scale runs with modifications are shown below, for procedures not including step c) recrystallization. Parameters and results for both steps b) and c) for some runs are presented in Example 3 after recrystallizations are complete.

| Entry | Input of (II) (g) | Cool Ramp (° C.) | Yield (III) (%) | Chemical purity by HPLC (%) | % de by chiral HPLC (%) | D content at chiral center by ¹H NMR (%) |
|---|---|---|---|---|---|---|
| 1 | 16 | 55→20 | 48 | 100 | 64.9 | 99.8 |
| 2 | 50 | 55→25 | 44 | 99.8 | 65.1 | 99.8 |
| 3 | 20 | 55→25 | 51 | 99.8 | 63.4 | 99.5 |
| 4 | 20 | 55→25 | 60 | 99.5 | 49.1 | 99.4 |
| 5 | 300 | 55→25 | 46 | 99.9 | — | 99.5 |
| 6 | 16.0 | 60→20 | 40 | 99.9 | 70.5 | 100 |

In entry 1, conditions for the diastereomeric salt formation procedure were fine-tuned from (II) to (III) crude by shifting the hold point to 55° C. instead of 60° C.; in this way much more crystallization occurred during this hold point; further cooling down was performed stepwise, with test-filtrations at 30° C. and 25° C., completely isolated at 20° C.

In entry 2, the optimized temperature ramp was tested again, with isolation at 25° C.; additionally use-test of new delivery of MeOD; slightly lower yield than entry 1 but good quality.

In entry 3, similar conditions to entry 2 were applied but longer aging time (36 h instead of 16 h) prior to filtration of product, significantly better yield and good quality obtained.

In entry 4, slightly less MeOD (90% the normal amount) was used to check the impact on yield and quality; yield is significantly improved, purity, especially chiral purity is significantly lower.

In entry 6, lower amount (0.6 eq instead of 1.0 eq) of dibenzoyl tartrate was tested, yield is slightly lower but (chiral) purity is comparable.

Example 3—Recrystallization of Enantioenriched (R)-Deuterated Pioglitazone L-Dibenzoyl Tartrate Salt (Compound (III) to Recrystallized Compound (III'))

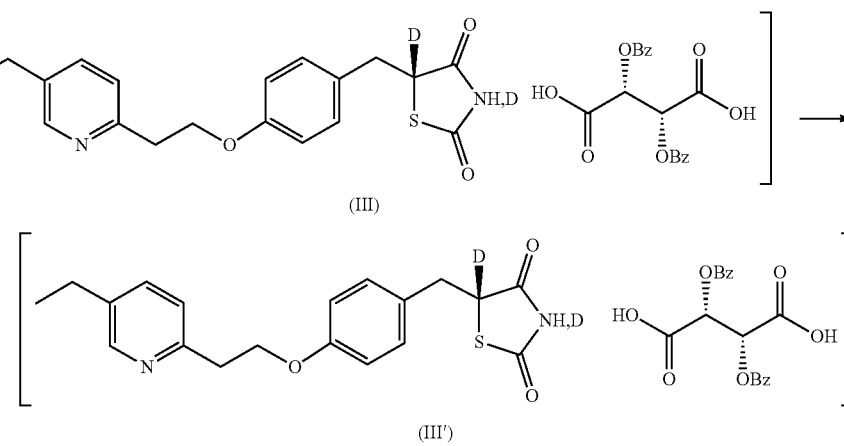

Example Run.

To prepare HCL salt: 46.88 kg enantioenriched (R)-deuterated pioglitazone dibenzoyl tartrate salt (compound (III)) was charged in a 1000 L glass vessel, followed by 185.6 kg MeOH (234.4 L; 4.0 w/w equivalents), 55.0 kg $D_2O$ (49.7 L; 1.17 w/w equivalents), and 7.1 kg 35% DCl in $D_2O$ (5.6 L; 0.15 w/w equivalents). The reaction mixture was warmed to 60 to 70° C. (63° C. achieved), and 218.0 kg $D_2O$ (196.9 L; 4.65 w/w equivalents) was added. The reaction was warmed to 70 to 80° C., and the mixture was stirred at that temperature for at least 30 minutes. An almost clear solution was obtained. The mixture was then cooled to 55° C. during 85 min. [Cooling time should be at least one hour]. The mixture was then stirred for at 55° C. for 120 min and seed crystals of (III') (0.14 kg) were added [Stirring can be performed at 52-58° C. for at least 2 hours during which time seed crystals of compound (III) or (III') could be added if desired]. The suspension was cooled to 26° C. over 10 h 50 min [Cooling ramp to 22 to 28° C. should be at least 5 hours long]. Then the suspension was stirred at 25° C. for 34 h 20 min [Suspension should be stirred for at least 15 hours at 22 to 28° C.]).

The product was filtered off on a stainless-steel centrifuge, and was washed with a premixed mixture of $D_2O$ (17.1 kg; 15.5 L; 0.36 w/w equiv) and MeOD (12.3 kg; 15.5 L; 0.26 w/w equiv). The product compound (III') was blown dry in a steam of nitrogen for at least 1 h. The product was then submitted to HPLC for measurement of optical purity. If optical purity was adequate (above 91%), (III') was dried in vacuo at a maximum temperature of 600 on a Hastelloy vacuum tray dryer. If not, a second recrystallization was performed (actual example: 93% ee; no second recrystallization). Deuterium NMR showed approximately 2 deuteriums per molecule.

Figure 3A:
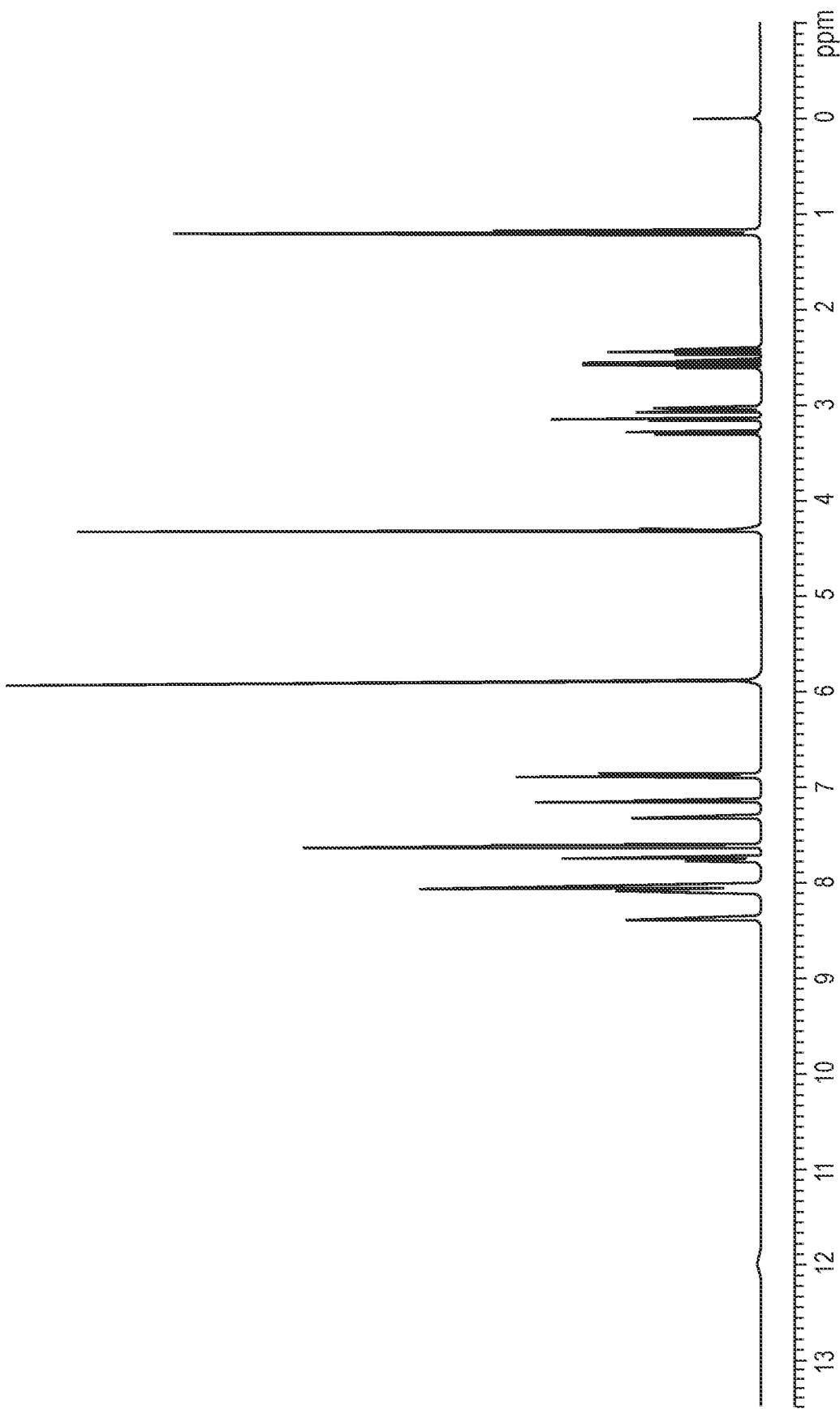
FIG. 3A depicts a $^1$H-NMR spectrum of compound (III') in DMSO-d6.
Figure 3B:
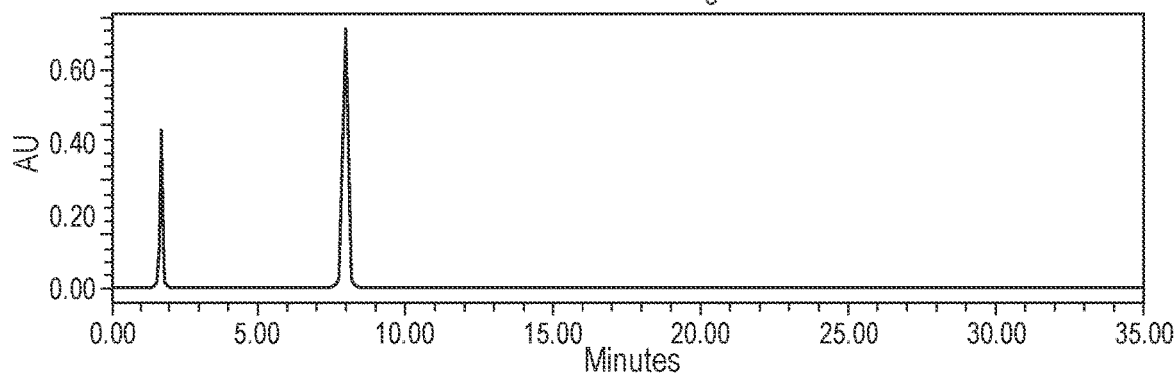
FIG. 3B depicts an LC trace showing chemical purity of compound (III')
Figure 3B:
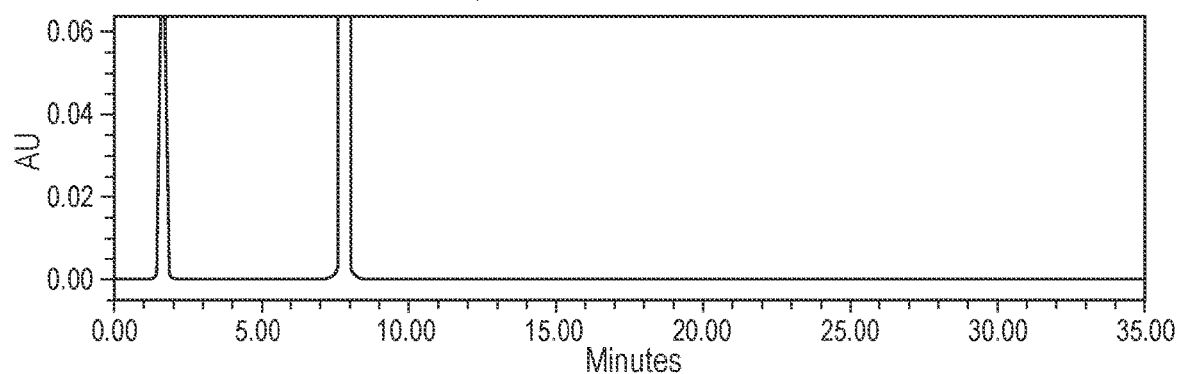
Figure 3C:
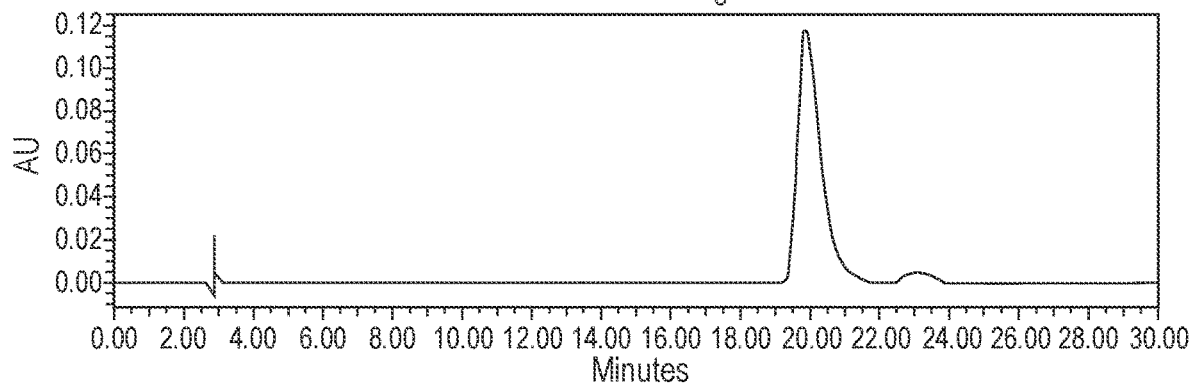
FIG. 3C depicts an LC trace showing optical purity of compound (III')
Figure 3C:
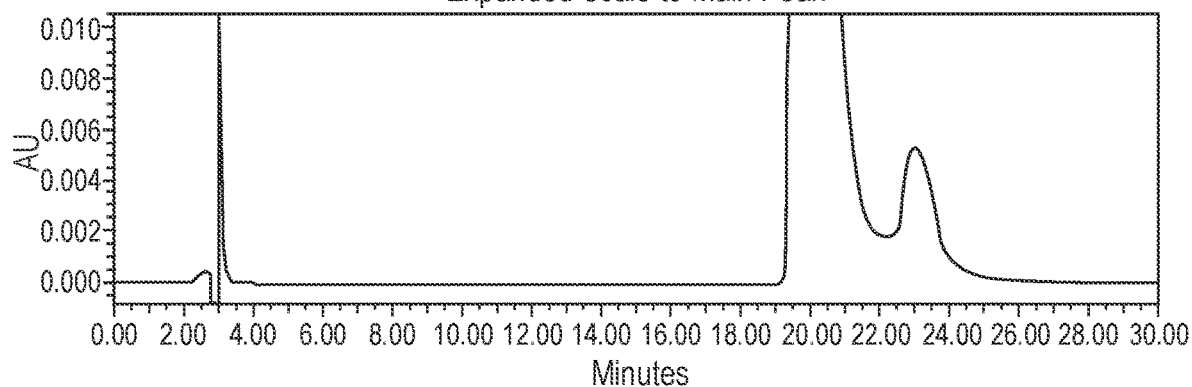

If a second or further recrystallizations are necessary, the above procedure can be repeated and the recrystallized material separated and dried in vacuo at a maximum temperature of 600 on a Hastelloy vacuum tray dryer as described above. Example analysis data can be found in FIGS. 3A, 3B, and 3C.

It should be noted that the details below include the procedures of both Example 2 and Example 3 (steps b) and c)).

To prepare the DCl salt, only deuterated solvents are used.

| Kilo scale runs | | | | | | |
|---|---|---|---|---|---|---|
| Entry | Input of (II) (kg) | Cool Ramp (° C.) | Yield $1^{st}$ recryst (%) | Yield of (III') final (%) | Chemical purity by HPLC (%) | % de by chiral HPLC (%) | D content at chiral center by $^1$H NMR (%) |
| K-1 | 58.60 | 60→20 | 16.8 | 16.8 | 99.5 | 96.7 | — |
| K-2 | 46.88 | 55→25 | 53.3 | 53.3 | 99.9 | 92.6 | 98 |
| K-3 | 35.02 | 60→20 | 45** | 28 | 99.5 | 96.6 | 98.5 |

For K-2: Color white to off-w lite; Appearance solid; $^1$H-NMR consistent with structure, deuteration grade (by $^1$H-NMR) 98%; purity (% area by HPLC) 99.9%; impurities 0.09%; loss on drying 0.44%.
**For K-3: was recrystallized three times, yield for $2^{nd}$ recrystallization was 76%, yield from third recrystallization was 82%. Yield and analysis data are for final product after $3^{rd}$ recrystallization

| Laboratory Scale runs with modifications | | | | | | | |
|---|---|---|---|---|---|---|---|
| Entry | Input of (II) (g) | Cool Ramp (° C.) | Yield $1^{st}$ recryst (%) | Yield $2^{nd}$ recryst. (%) | Yield (III') final (%) | Chemical purity by HPLC (%) | de by chiral HPLC (%) | D content at chiral center by $^1$H NMR (%) |
| 1 | 14.25 | 75→25 | 51 | 73 | 17 | 99.6 | 94.8 | 100 |
| 2 | 16.0 | 60→25 | 56 | 72 | 17 | 99.4 | 96.4 | 92.8 |
| 3 | 16.0 | 60→20 | 56 | 76 | 15 | 99.7 | 96.0 | 94.4 |
| 4 | 16.0 | 60→22 | 58 | 74 | 20 | 99.5 | 96.4 | 98.9 |
| 5 | 16.0 | 60→20 | 38/87 | 78/95 | 16/44 | 99.3/99.7 | 93.8/72.3 | >99/98.3 |
| 6 | 16.0 | 60→8 | 84 | 85 | 38 | 97.5 | 65.9 | 99.0 |
| 7 | 12.0 | 60→22 | 58 | 78 | 22 | 99.4 | 97.5 | 99.2 |
| 8 | 16.0 | 60→20 | 65 | 80 | 23 | 99.9 | 98.9 | 97.4 |
| 10 | 120 | 60→20 | 91 | 74 | 21 | 99.7 | 98.8 | 99.3 |
| 11 | 9.34 | 60→20 | 65 | — | 24 | 99.9 | 86.5 | 99.2 |
| 13 | 15.0 | 60→20 | 55 | 82 | 45 | 99.7 | 95.2 | 98.4 |
| 14 | 40 | 60→20 | 53 | 78 | 41 | 99.7 | 95.7 | 98.5 |
| 15 | 80 | 60→20 | 50 | 78 | 39 | 99.7 | 95.5 | 98.7 |
| 17 | 40 | 60→20 | 52 | 79 | 41 | 99.7 | 95.4 | 98.8 |
| 18 | 10 | 60→20 | 53 | 76 | 40 | 99.7 | 95.1 | 98.3 |
| 19 | 20 | 55→25 | 63 | 82 | 51 | 99.6 | 96.7 | 97.3 |
| 20 | 20 | 55→25 | 55 | 79 | 44 | 99.6 | 98.0 | 97.3 |
| 21 | 20 | 55→25 | 56 | 78 | 43 | 99.9 | 97.5 | 96.9 |
| 22 | 350 | 55→25 | 60 | 72 | 43 | 99.9 | 97.4 | 98.0 |
| 23 | 20.0 | 55→25 | 56 | | 56 | 99.9 | 94.0 | 98.9 |

In entry 2, MeOH instead of MeOD was tested; additionally, stepwise cooling was applied (75→60° C./, 2 h hold point at 60° C., then to 25° C.); seed crystals of entry 1-material were added at the 60° C. hold point, no oiling but good crystallization occurred; decrease in deuteration grade was observed.
In entry 3, the experiment with MeOH was repeated, crystallization worked well with seeding and with the ramp; worked well, once again decrease in deuteration grade was observed.
In entry 4, another experiment with MeOD was performed, this time aging during initial salt formation was extended over the weekend to see whether this increases the yield; purity and % ee remain good.
In entry 5, less solvent (80% of both MeOD as well as $D_2O$) was tested; at the beginning at 75° C. it remained far from clear solution; after initial salt formation the amount was divided, half was re-crystallized with 80% solvent (first set of numbers); other half was re-crystallized without DCl (second set of numbers: in this way it remained a suspension during re-crystallization.
In entry 6, it was tried to cool down to a lower temperature (5 to 10° C. instead of 20 to 25° C.) to increase the yield; product came out much more sticky/oily, yield is higher but quality and especially chiral purity is much lower.
In entry 7, the first batch of (II) and the new batch of tartrate were use-tested; worked very well, best yield and best chiral purity so far.
In entry 8, a 1:1 mixture (v/v) of MeOD and MeOH was tested; after the first crystallization D-grade reduced from 99.4% to 97.4% already, otherwise good quality.

| | | | Laboratory Scale runs with modifications | | | | |
|---|---|---|---|---|---|---|---|
| Entry | Input of (II) (g) | Cool Ramp (° C.) | Yield 1$^{st}$ recryst (%) | Yield 2$^{nd}$ recryst. (%) | Yield (III') final (%) | Chemical purity by HPLC (%) | de by chiral HPLC (%) | D content at chiral center by $^{1}$H NMR (%) |

In entry 10, a larger scale reaction under standard conditions was performed to produce sufficient seed crystals for the first batch in production.
In entry 11, standard conditions were tested with MeOD/H₂O for initial salt formation and all protonated solvents for re-crystallization: at rt no clear solution was obtained as described, heating to 60° C. was necessary to get clear solution; good deuterium content but poor chiral purity and yield obtained.
In entry 13, (III) was re-crystallized similar to entry 8 from example 2, with MeOD/MeOH 1:1 (v/v); still good deuteration grade obtained, chiral purity is close to limit.
In entry 14, the conditions of entry 13 were repeated, showing that MeOD/MeOH 1:1 really reliably gives good deuteration grade, chiral purity is close to limit.
In entry 15, the conditions of entry 13 or 14 were repeated again, on somewhat larger scale, chiral purity is close to limit.
In entry 17, similar conditions to entries 13 to 15 were tested, but with MeOD/MeOH 3:7; still gives good deuteration grade.
In entry 18, similar conditions to entry 17 were applied but with pure MeOH, still gives good deuteration grade.
In entry 19, the pure methanol conditions of entry 18 were used in combination with the cooling ramp developed for (III) (55° C. for seeding & aging; 25° C. final temperature & 15 h aging time) in this way good yield could be obtained.
In entry 20, another experiment similar to entry 19 was completed.
In entry 23 only one recrystallization is providing an enantiomeric excess still high knowing that a recrystallization can be applied in HCl or DCl salt last step formation.

Example 4—Preparation of Enantioenriched (R)-Deuterated Pioglitazone (Compound (IV))

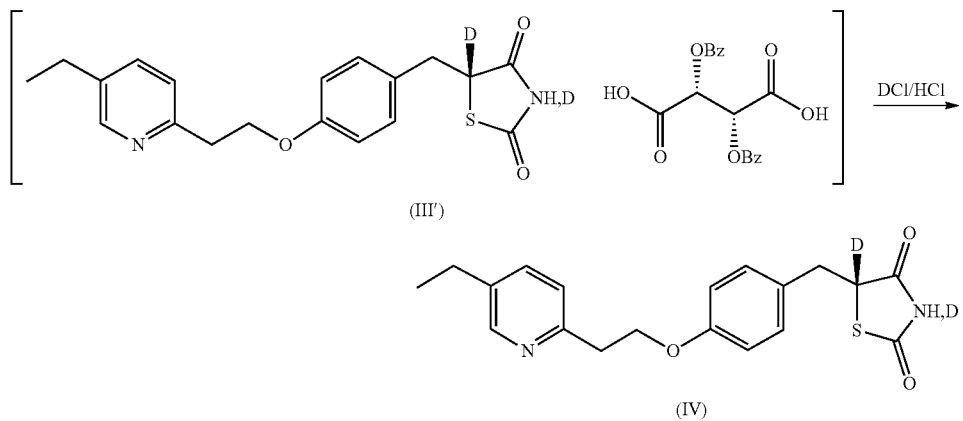

The synthesis started with dissolving recrystallized compound (III') in methanol and 35% DCl in D₂O at elevated temperature. The almost clear solution was passed through a polish filter. Then ethyl acetate was added at elevated temperature and the reaction mixture was cooled slowly to a temperature from about 15 to about 25° C. and further stirred at 15 to 25° C. An in-process control (IPC) for chiral purity was performed. Depending on the result of the IPC, the sequence could be repeated a second time (with a smaller amount of DCl) to further increase the chiral purity. Eventually, the product was filtered off, washed with ethyl acetate, and dried in vacuo.

Example Run 24.62 kg recrystallized compound (III') was charged in a 600 L glass vessel, followed by 97.5 kg MeOH (123.1 L; 4.0 w/w equivalents), and 11.5 kg 35% DCl in D₂O (9.1 L; 0.47 w/w equivalents). The reaction mixture was warmed to a temperature from about 50 to about 60° C. (55° C. achieved), and the mixture was stirred at that temperature for at least 30 minutes. The mixture was then filtered over a polish filter into a 1000 L glass vessel and the filter was rinsed with 9.7 kg methanol (12.3 L; 0.40 w/w equivalents) at 50 to 60° C. (55° C. achieved).

369.8 kg of ethyl acetate (410.4 L; 15.8 w/w equivalents) was charged into the vessel at 50 to 60° C., and the mixture was then cooled to 25° C. over 145 min [Cooling ramp to a temperature from about 15 to about 25° C. should be at least two hours long]. The mixture was then stirred at 21° C. for 120 min [Stirring can be performed at 15 to 25° C. for at least 2 hours]. The product was filtered off on a Hastelloy nutsche filter and the product was washed with 44.37 kg ethyl acetate (49.24 L; 1.8 w/w equivalents).

The product compound (IV) HCl salt was blown dry in a steam of nitrogen for 3 h [Drying should be performed for at least 30 min]. Deuterium NMR showed approximately 1 deuterium per molecule; thus, the thiazolidinedione nitrogen has a hydrogen attached and the salt is an HCl salt. The product was then submitted to IPC for measurement of optical purity. In this example a 94.9% ee was measured and the decision was made to perform a second recrystallization [If adequate optical purity (for example above 98% or above 96% ee) is obtained, the compound is dried in vacuo at a maximum temperature of 600 on a Hastelloy vacuum tray dryer].

Figure 4A:
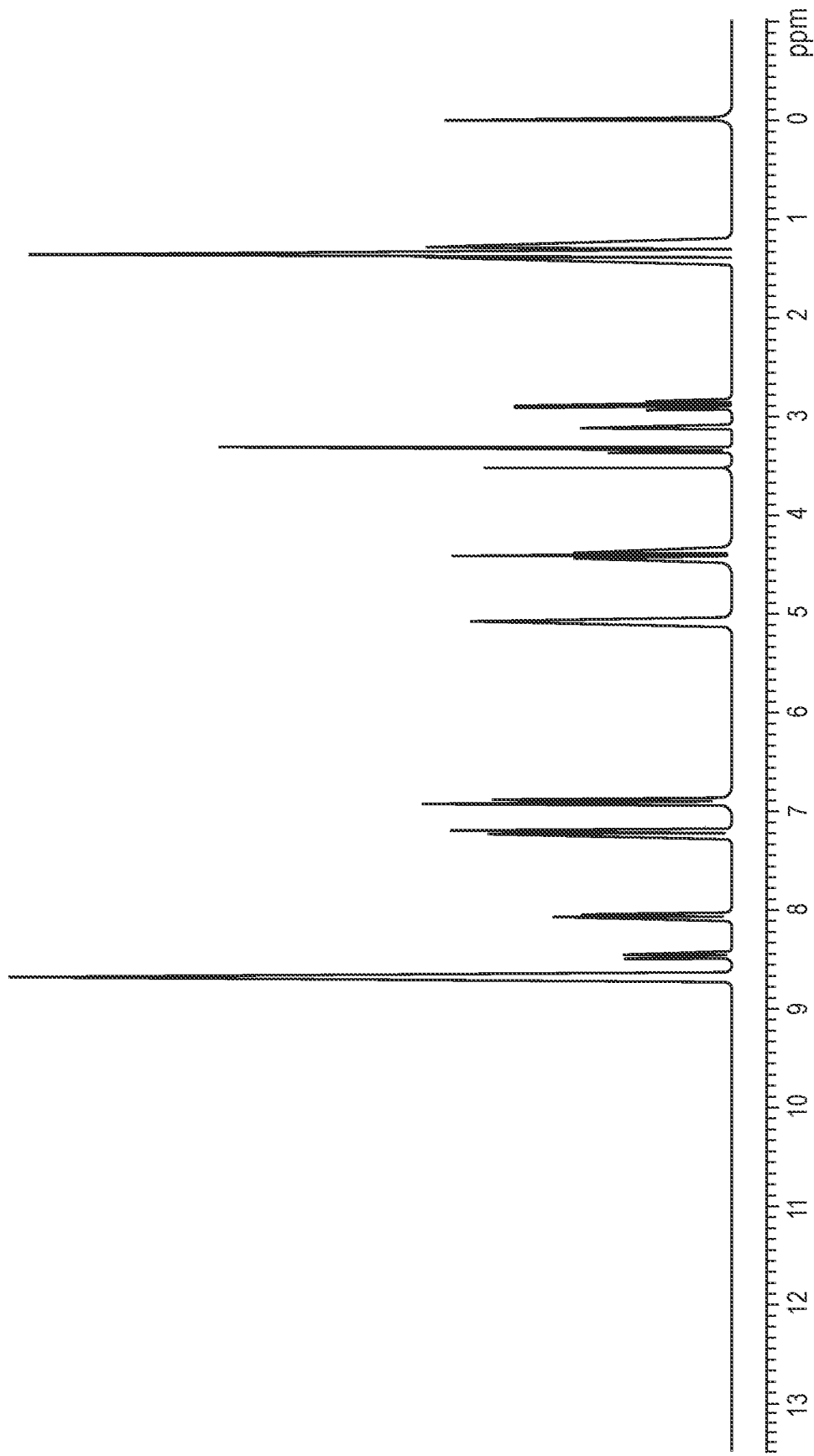
FIG. 4A depicts a $^1$H-NMR spectrum of compound (IV) in DMSO-d6.
Figure 4B:
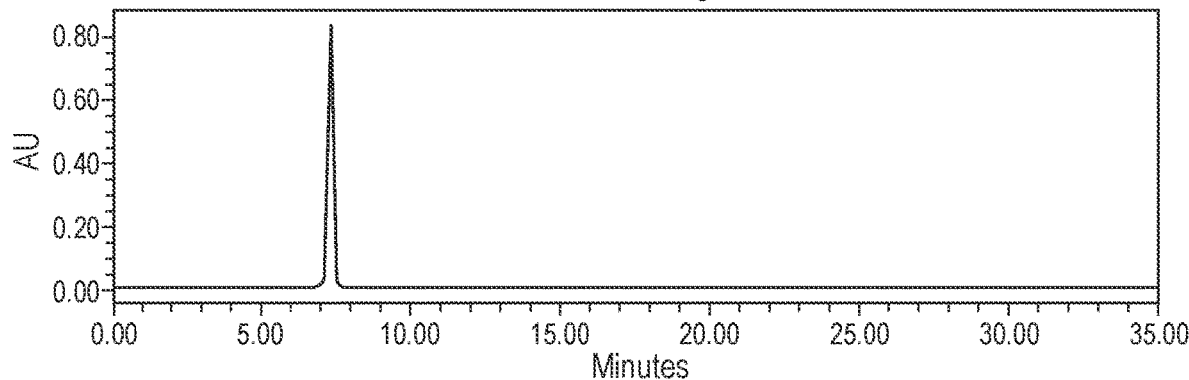
FIG. 4B depicts an LC trace showing chemical purity of compound (IV)
Figure 4B:
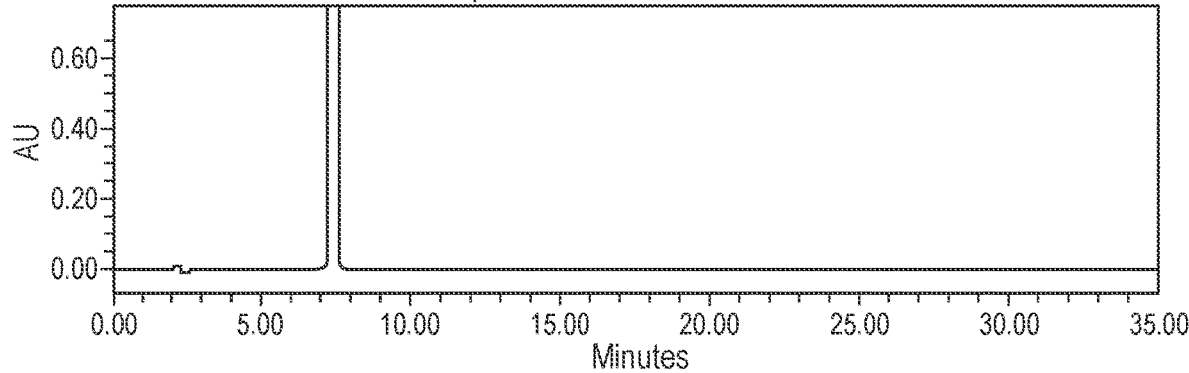
Figure 4C:
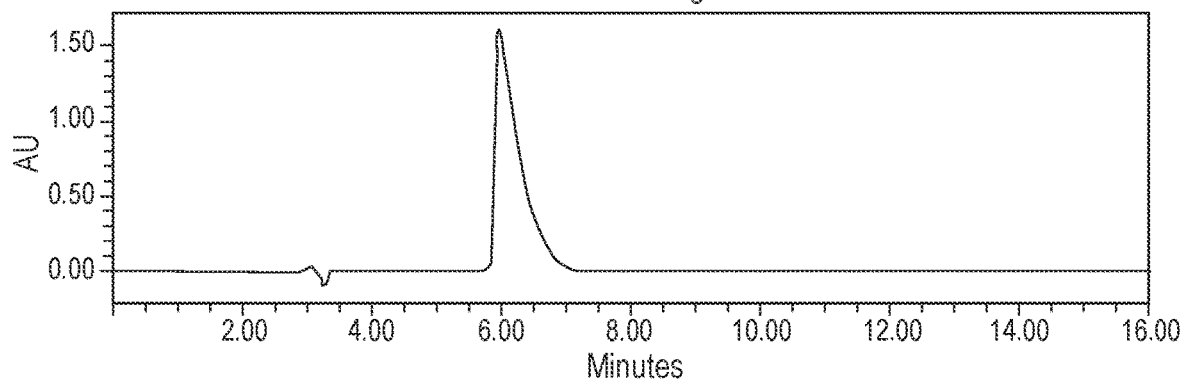
FIG. 4C depicts an LC trace showing optical purity of compound (IV)
Figure 4C:
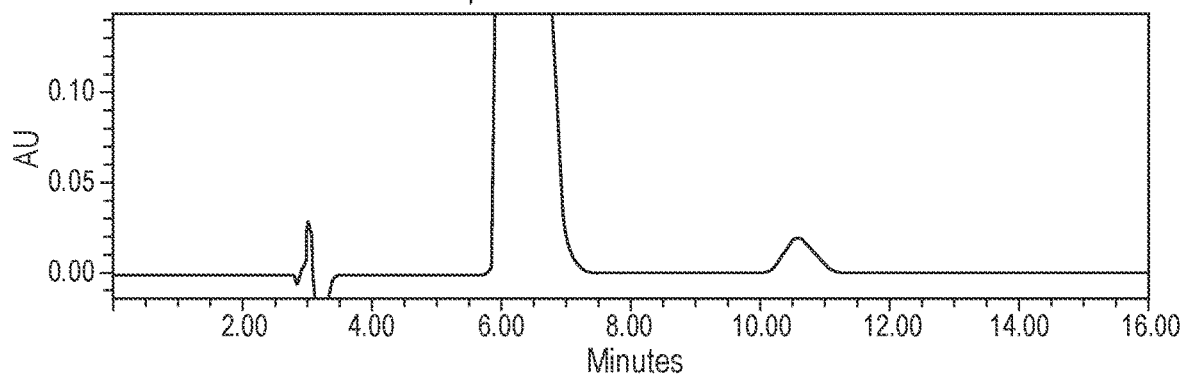

A second crystallization can be performed as follows:

11.82 kg of moist crude crystallized compound (IV) from the first crystallization was charged in a 600 L glass vessel, followed by 83.8 kg MeOH (105.9 L; 7.09 w/w equivalents), and 1.5 kg 35% DCl in $D_2O$ (1.2 L; 0.13 w/w equivalents). The reaction mixture was warmed to 50 to 60° C., and the mixture was stirred at that temperature for at least 30 minutes. The mixture was then filtered over a polish filter into a 1000 L glass vessel and the filter was rinsed with 7.8 kg methanol (9.8 L; 0.66 w/w equivalents) at 50 to 60° C. 315.0 kg of ethyl acetate (349.6 L; 26.6 w/w equivalents) was charged into the vessel at 50 to 60° C., and the mixture was then cooled to 21° C. over 150 min [Cooling time to 15 to 25° C. should be at least two hours]. The mixture was then stirred at 21° C. for 120 min [Stirring at 15 to 25° C. should be at least 2 hours]. The product was then filtered off on a Hastelloy nutsche filter and the product was washed with 14.64 kg ethyl acetate (49.24 L; 1.24 w/w equivalents). The product compound (IV) HCl salt was blown dry in a steam of nitrogen for 42 min [Drying should be at least 30 min]. Deuterium NMR showed approximately 1 deuterium per molecule; thus, the thiazolidinedione nitrogen has a hydrogen attached and the salt is an HCl salt [A DCl salt would be produced if DCl is used and if solvents are predominantly deuterated]. The product was then submitted to IPC for measurement of optical purity (actual example measurement: 96.9% ee). The product was dried in vacuo at a maximum temperature of 600 on a Hastelloy vacuum tray dryer until the MeOH and ethyl acetate levels (measured by gas chromatography) were below 3000 ppm and 5000 ppm, respectively. Example analysis data can be found in FIGS. 4A, 4B, and 4C.

| | Kilo scale runs | | | | | |
|---|---|---|---|---|---|---|
| Entry | Input of (III') (kg) | Ratio MeOH/ EtOAc (v/v) | Yield of (IV) (%) | Chemical purity by HPLC (%) | % ee (enantiomeric excess) by chiral HPLC (%) | D content at chiral center by $^1$H NMR (%) |
| K-1 | 9.6 | 1:3 | 85 | 99.7 | | |
| K-2 | 4.46 | 1:3 | 82 | 99.8 | 97.1 | 97.0 |
| K-3 | 24.62 | 1:3 | 53.3 | 99.9 | 97.0 | |

For entry K-1: only first recrystallization performed, DCl salt formation. RRT = 1.41 is higher than specified
For entry K-2: K-1 batch was recrystallized; RRT = 1.41 is reduced (didehydropioglitazone or impurity B)
For entry K-3: initial recrystallization showed 94.9% ee, then second recrystallization performed;

Other data for entry K-3: Color white to off-white; Appearance powder; $^1$H-NMR consistent with structure; HPLC retention time conforms to structure; Organic impurities: non-deuterated pioglitazone 3.2%, deuterated S-pioglitazone 1.5%, didehydropioglitazone <LOQ; total impurities 4.7%; deuteration grade (by $^1$H-NMR) 97%; water content (KF oven method corr. USP<921>method LC) 0.01%; residual solvents by GC: methanol 72 ppm, ethyl acetate 323 ppm.

| | Laboratory Scale runs with modifications | | | | | |
|---|---|---|---|---|---|---|
| Entry | Input of (III') (g) | Ratio MeOH/ EtOAc (v/v) | Yield of (IV) (%) | Chemical purity by HPLC (%) | ee by chiral HPLC (%) | D content at chiral center by $^1$H NMR (%) |
| 1 | 4.0 | 1:3.3 | 71 | 99.6 | 96.1 | 100 |
| 2 | 4.0 | 1:3.3 | 85 | 99.6 | 97.3 | 92.6 |
| 3 | 7.5 | 1:3.3 | 85 | 99.9 | 97.7 | 97.5 |
| 4 | 4.0 | 1:2.5 | 78 | 99.8 | 97.2 | 98.3 |
| 5 | 4.0 | 1:2.0 | 77 | 99.8 | 97.2 | 98.0 |
| 6 | 4.0 | 1:4.0 | 83 | 99.8 | 97.0 | 98.2 |
| 7 | 50 | 1:3.3 | 85 | 99.7 | 97.4 | 97.9 |
| 8 | 10 | 1:3.3 | 81 | 99.8 | 95.0 | 98.8 |
| 9 | 4.0 | 1:3.3 | 86 | 99.9 | 96.8 | 98.0 |
| 11 | 20 | 1:3.3 | 89 | 99.7 | 96.9 | 97.4 |
| 13 | 10.0 | 1:3.3 | 87 | 99.8 | 97.4 | 96.5 |
| 14 | 10.0 | 1:3.3 | 88 | 99.9 | 97.0 | 97.1 |
| 15 | 10.0 | 1:3.3 | 87 | 99.9 | 95.1 | 98.1 |
| 16 | 4.8 | 1:3.3 | 91 | 100 | 97.0 | 97.7 |
| 17 | 40 | 1:3.3 | 71 | 100 | 96.7 | 97.1 |

*starting material was not compound (III'), but was the tartrate salt of pioglitazone with no deuterium
In entry 1, no clear solution was obtained. During the polish filtration, a small amount of solids was removed. After addition of EtOAc and upon cooling, the product crystallized out nicely and good quality was obtained (based on starting material (III'))
In entry 2, MeOH was tested instead of MeOD; deuteration grade on chiral center remained (but was already low at compound (III') stage), ee was slightly increased.
In entry 3, MeOH and HCl were used, starting with (III') with good/high D-grade, remained high, chemical purity and chiral purity on API was high.
In entries 4 to 6, similar conditions to entry 3 were applied with respect to use of MeOH and HCl but the ratio of MeOH to EtOAc was varied; a slight impact on the yield and almost no impact on purity were observed.
In entry 7, the batch of (III') was use-tested with the finalized procedure before starting kilolab trial: MeOH but DCl and MeOH/EtOAc ratio 1:3.3.
In entry 8, an IPC sample of the batch after 2 recrystallizations was converted to (IV) to check what kind of quality would have been reached w/o third re-crystallization; as expected the chiral purity is below specification limit, but the chemical purity is better than entry 7 (rrt = 1.41 is lower).
In entry 9, the material of entry 8 was re-crystallized to check whether the chiral purity can be further improved; indeed chiral purity (and also chemical purity) does improve.
In entry 1,1 the batch of (IV) was re-crystallized, similar to entry 9 to check whether the rrt =1.41 impurity can be depleted.
In entry 13 (III') with 97.1% D-grade was converted to (IV) using MeOH; D-grade is slightly eroded to 96.5% (analytical variation also linked to analysis by NMR $^1$H is not taken in account).
In entry 14, the same (III') with 97.1% D-grade is converted to (IV) using MeOD; in this way the D-grade remains at 97.1%.
In entry 15 (III'), which was re-crystallized only once was converted to (IV) to check what kind of quality can be obtained in this way (most likely better D-grade and chemical purity but due to low ee, re-crystallization of (IV) needed, but afterwards still better D-grade and chemical purity should be obtained than if (III') was re-crystallized a 2nd time).
Entry 16 describes the recrystallization of the entry 15 product.

Example 5—Synthesis of (R)-5-({4-[2-(5-ethyl-2-pyridyl)ethoxy]phenyl}methyl)-(3,5-$^2$H$_2$)-1,3-thiazolidine-2,4-dione deuterium chloride salt (dideutero-(R)-pioglitazone·DCl; Compound (IVa))

1. $D_2O$, 100° C. (twice)
2. L-DBTA (1 eq)/MeOD/$D_2O$
3. MeOD, DCl, $D_2O$ (twice)
4. MeOD, DCl, EtOAc (I)

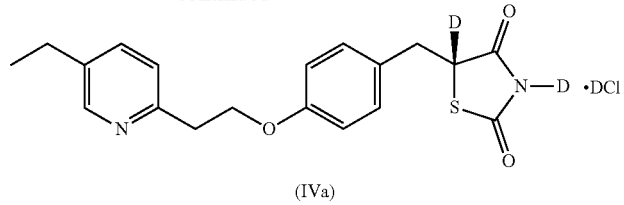

(IVa)

Hydrogen/Deuterium (HID) Exchange (RS)-$^2$H$_2$-pioglitazone DCl was obtained from compound (I) following the process described in example 1. The yield after the 2 cycles of H/D exchange was close to 90%. Two batches were prepared with a D-content at the chiral center of 99.0 and 99.4 atom % as determined by $^1$H NMR in DMSO-d$_6$.

Classical Resolution of (RS)-$^2$H$_2$-Pioglitazone DCl Salt

Deuterated (R)-pioglitazone L-DBTA salt was prepared in four batches according to the process described in example 2, as summarized below:

For each batch, (RS)-$^2$H$_2$-pioglitazone DCl (142.5 g; 360.9 mmol) and L-DBTA (136 g; 361.4 mmol; 1 equiv.) were added to 950 g MeOD and the mixture was heated to 60° C. D$_2$O (1425 g) was then slowly added and the solution was heated to 75° C. The mixture was allowed to cool to ambient temperature and was stirred overnight. The crystals that formed were collected by filtration and washed with 250 mL MeOD/D$_2$O (1:1 v/v). After drying, each batch gave:
Batch 1: 146.6 g; 52.6% yield; 53.0% de,
Batch 2: 141.3 g; 55.8% yield; 55.4% de;
Batch 3: 139.7 g; 52.7% yield; 57.2% de;
Batch 4: 146.0 g; 53.6% yield; 55.6% de.

Recrystallization of Deuterated (R)-Pioglitazone L-DBTA Salt

Recrystallization of deuterated (R)-pioglitazone L-DBTA salt was performed in two batches according to the process described in example 3 using only MeOD (as mentioned earlier, the use of deuterated solvents is required to ensure the highest D incorporation in the molecule). In this example, each batch was recrystallized a second time to reach a diastereomeric excess compatible with target specifications.

1st recrystallization: For each of the two batches, a mixture of (R)-enantiomer-enriched $^2$H$_2$-pioglitazone·L-DBTA (280 g; 391 mmol), 42 g of 35% DCl in D$_2$O, 1150 g MeOD, and 330 g D$_2$O was heated until a clear solution was obtained (60° C.). D$_2$O (1300 g) was then added and the mixture was reheated to 65° C. The slightly turbid solution was cooled to ambient temperature and stirred overnight. Crystallization started at around 50° C. The crystallized material was isolated by filtration and washed with 250 mL of D$_2$O/MeOD (1:1 v/v). After drying, 163.9 g solid was obtained for batch 1 (58.5% yield; 92.1% de) and 165.5 g solid was obtained (59.1% yield; 91.8% de) for batch 2.

2nd recrystallization: For each batch described above, a mixture of (R)-enantiomer-enriched $^2$H$_2$-pioglitazone·L-DBTA (160 g; 224 mmol), 24 g of 35% DCl in D$_2$O, 640 g MeOD, and 200 g D$_2$O was heated until a clear solution was obtained (60° C.). D$_2$O (850 g) was then added and the mixture was reheated to 65° C. The slightly turbid solution was cooled to ambient temperature and stirred overnight. The crystallized material was isolated by filtration and washed with D$_2$O/MeOD (1:1 v/v). After drying, 118.7 g solid was obtained (74.2% yield of the second recrystallization; diastereomeric excess of wet cake: 98.6% de) for batch 1 and 124.3 g solid was obtained (77.7% yield of the second recrystallization; diastereomeric excess of wet cake: 99.3% de) for batch 2.

Synthesis of (R)-$^2$H$_2$-pioglitazone·DCl (Compound (IVa))

As mentioned in example 4 describing the synthesis of (R)-$^2$H$_2$-pioglitazone·HCl salt using non-deuterated methanol; a DCl salt can be obtained if solvents are predominantly deuterated as shown in the example below:

A mixture of twice-recrystallized (R)-enantiomer-enriched $^2$H$_2$-pioglitazone·L-DBTA (240 g; 336 mmol; deuterium content >99 atom %; diastereomeric excess 99% de), 1200 mL of MeOD, and 2.9 equiv. of concentrated DCl in D$_2$O (2.9 equiv.) was heated to 50° C. The slightly turbid solution was filtered over a 0.45 µm filter and the filtrate was reheated to 50° C. Ethyl acetate (4000 mL) was then added and the mixture was allowed to cool to 20° C. After stirring for 2 hours at this temperature, the crystalline (R)-$^2$H$_2$-pioglitazone·DCl was isolated by filtration. After washing with ethyl acetate, 122 g of wet cake (enantiomeric excess: 98.9% ee) was isolated. After drying overnight at 50° C. in vacuo, 119.3 g of compound (IVa) as white crystalline material was obtained. Analytical data for the final product is presented in Table 1 below.

TABLE 1

| Analytical data* for (R)-$^2$H$_2$-pioglitazone.DCl (Compound (IVa)) | |
|---|---|
| | Result |
| Enantiomeric excess [%; determined by chiral HPLC] | 98.1 |
| D content at chiral center [%; determined by $^1$H-NMR] | 99.1 |
| Assay (by HPLC) | 99.9 ± 1 |

*Analytical results by HPLC were obtained using USP pharmacopeia methods for Pioglitazone Hydrochloride (United States Pharmacopeial Convention Official Monographs, May 1, 2015, pages 4886-4887)
Deuterium content was determined by quantitative deuterium NMR, which showed close to 3 deuteriums per molecule (chiral center, DCl, and N-D based on the exchangeable nature of the hydrogen at the N-H in keeping with its pKa value)

INCORPORATION BY REFERENCE

All references listed herein are individually incorporated in their entirety by reference.

EQUIVALENTS

Numerous modifications and variations of the invention are possible in light of the above teachings. It is therefore to be understood that within the scope of the appended claims, the invention may be practiced otherwise than as specifically described herein.

The invention claimed is:

1. A method of producing compound (IV) or salt thereof, the method comprising the steps:

a) reacting compound (I) or salt thereof with D₂O and DCl at a temperature from about 80° C. to about 100° C. to produce compound (II) or salt thereof

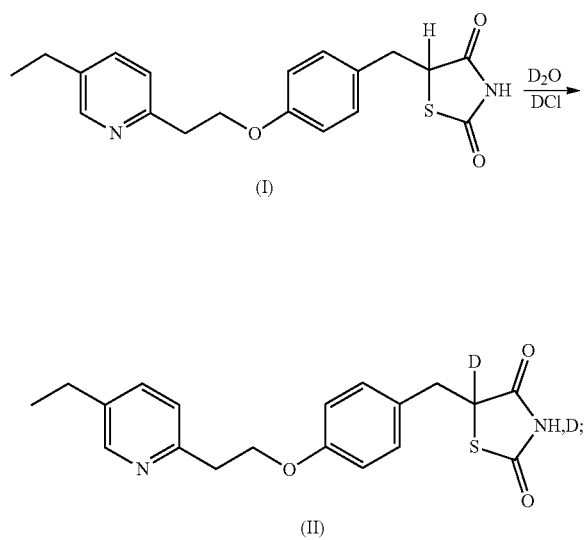

b) reacting compound (II) or salt thereof with L-dibenzoyl tartaric acid in a first solvent comprising at least 90% by volume of MeOD and/or MeOH, or at least 90% by volume of a mixture of MeOD and/or MeOH, and D₂O to produce compound (III)

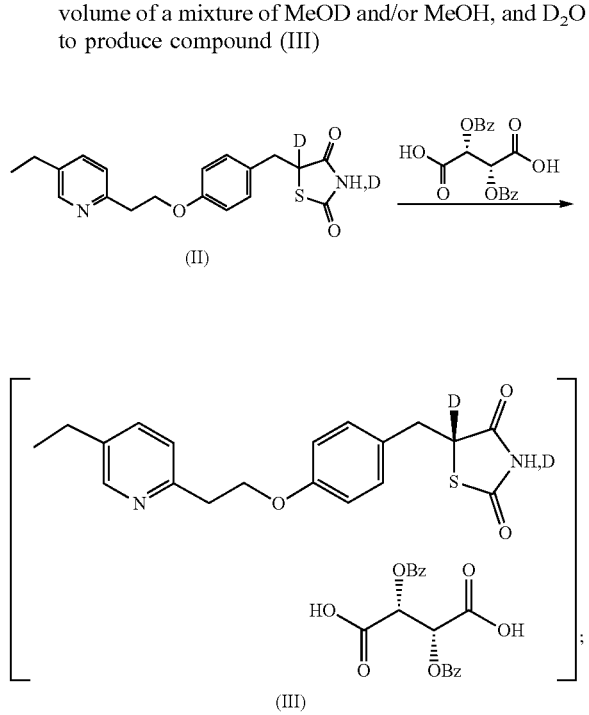

c) recrystallizing compound (III) one or more times in a second solvent comprising at least 90% by volume of a mixture of D₂O, DCl and/or HCl, and MeOH and/or MeOD to produce recrystallized compound (III')

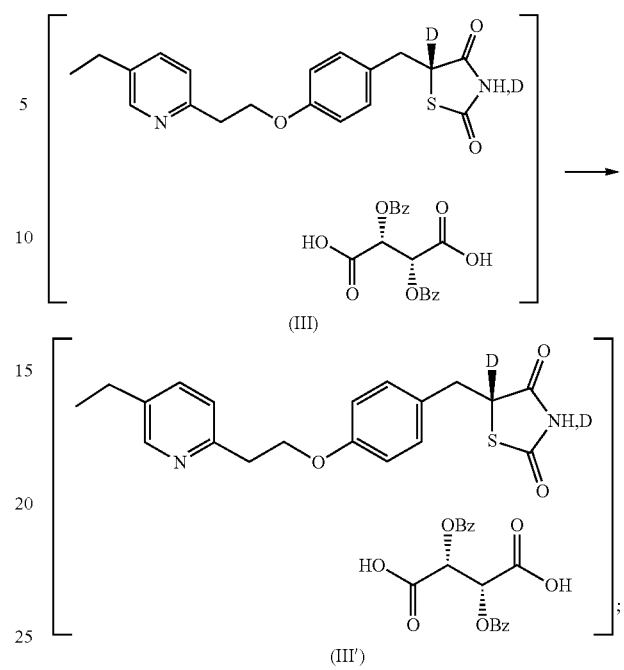

and d) reacting recrystallized compound (III') with DCl and/or HCl, in a third solvent which comprises deuterated and/or non-deuterated solvent, to produce compound (IV), or salt thereof, which is obtained by crystallization

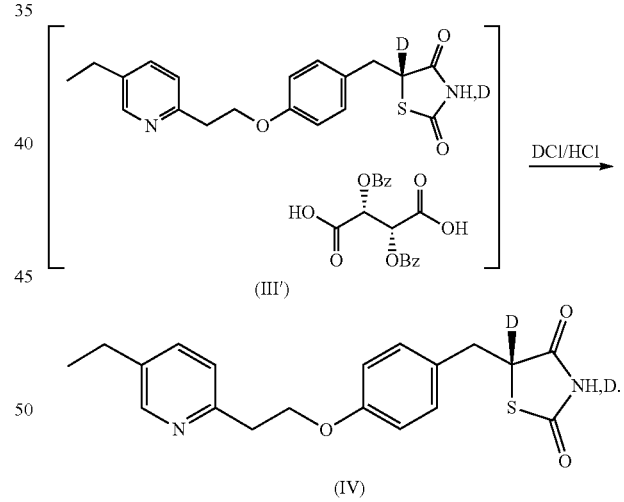

2. The method of claim 1, further comprising wherein step a) is repeated in multiple cycles, and wherein in step a) a mother liquor from a second or subsequent cycle is resubjected to the step a) conditions to obtain additional compound (II) or salt thereof.

3. The method of claim 1, wherein the volume of D₂O in step a) is from about 3 to about 8 volumes w/w based on the weight of compound (I) or salt thereof.

4. The method of claim 1, wherein in step a) the reaction mixture further comprises toluene, and the ratio of D₂O to toluene is from 1:3 to 3:1 by volume.

5. The method of claim 1, wherein in step b) the molar amount of L-dibenzoyl tartaric acid is from about 0.6 to about 3 molar equivalents based on the molar amount of compound (II) or salt thereof.

6. The method of claim 5, wherein in step b) the molar amount of L-dibenzoyl tartaric acid is from about 0.6 to about 1 equivalent based on the molar amount of compound (II) or salt thereof.

7. The method of claim 1, wherein in step b) the first solvent is a mixture of $D_2O$ and MeOD in a $D_2O$/MeOD ratio of from about 1:3 to about 3:1 by volume.

8. The method of claim 1, wherein in step c) the ratio of MeOH to MeOD is from about 1:3 to about 3:1 by volume.

9. The method of claim 1, wherein the second solvent $D_2O$:(MeOD+MeOH) ratio is about 1:1 by volume.

10. The method of claim 1, wherein the second solvent $D_2O$ amount is from about 5 volumes w/w to about 10 volumes w/w and the (MeOD+MeOH) amount is from about 5 volumes w/w to about 10 volumes w/w based on compound (III).

11. The method of claim 1, wherein step c) is repeated in multiple cycles.

12. The method of claim 1, wherein in step d) the third solvent comprises MeOH and/or MeOD.

13. The method of claim 1, wherein the third solvent amount is from about 5 volumes to about 10 volumes w/w based on compound (III').

14. The method of claim 1, wherein in step d) the third solvent comprises at least 90% by volume of a mixture of a deuterated or non-deuterated hydroxylic solvent and a non-deuterated-non-hydroxylic solvent.

15. The method of claim 1, wherein in step d) compound (IV) is the HCl salt.

16. The method of claim 1, wherein the enantiomeric excess of compound (IV) or salt thereof is at least 95%, at least 96%, at least 97%, at least 98%, or at least 99%.

17. The method of claim 1, wherein the HPLC purity of compound (IV) or salt thereof is at least 91%, at least 95%, at least 96%, at least 97%, at least 98%, at least 99%, at least 99.5%, or at least 99.8%.

18. The method of claim 1, wherein the deuterium content at the chiral center of compound (IV) or salt thereof is at least 90%, at least 93%, at least 95%, at least 96%, at least 97%, at least 98%, or at least 99%.

19. The method of claim 1, wherein for compound (IV) or salt thereof the enantiomeric excess is at least 96%, wherein the deuterium content at the chiral center is at least 96%, and the HPLC purity is at least 98%.

20. The method of claim 2, wherein compound (IV) or salt thereof has at least 90% H attached to the thiazolidinedione nitrogen or at least 90% deuterium attached to the thiazolidinedione nitrogen.

\* \* \* \* \*